(12) United States Patent
Blin et al.

(10) Patent No.: US 8,992,903 B2
(45) Date of Patent: Mar. 31, 2015

(54) COMPOSITION COMPRISING AT LEAST ONE BLOCK POLYMER AND AT LEAST ONE GELLING AGENT

(75) Inventors: Xavier Blin, Paris (FR); Véronique Ferrari, Maisons-Alfort (FR)

(73) Assignee: L'Oreal, Paris (FR)

( * ) Notice: Subject to any disclaimer, the term of this patent is extended or adjusted under 35 U.S.C. 154(b) by 1809 days.

(21) Appl. No.: 10/528,835

(22) PCT Filed: Sep. 26, 2003

(86) PCT No.: PCT/FR03/02848
§ 371 (c)(1),
(2), (4) Date: Oct. 4, 2005

(87) PCT Pub. No.: WO2004/028486
PCT Pub. Date: Apr. 8, 2004

(65) Prior Publication Data
US 2006/0147402 A1    Jul. 6, 2006

(30) Foreign Application Priority Data

Sep. 26, 2002  (FR) ..................... 02 11949
Dec. 20, 2002  (FR) ..................... 02 16437
May 21, 2003   (FR) ..................... 03 06121

(51) Int. Cl.
| | | |
|---|---|---|
| *A61K 31/74* | (2006.01) |
| *C08L 51/00* | (2006.01) |
| *A61K 8/26* | (2006.01) |
| *A61K 8/81* | (2006.01) |
| *A61K 8/891* | (2006.01) |
| *A61K 8/90* | (2006.01) |
| *A61K 8/92* | (2006.01) |
| *A61Q 1/04* | (2006.01) |
| *A61Q 1/06* | (2006.01) |
| *A61Q 1/10* | (2006.01) |
| *A61Q 3/02* | (2006.01) |
| *C08F 265/04* | (2006.01) |
| *C08F 265/06* | (2006.01) |
| *C08F 291/00* | (2006.01) |
| *C08F 293/00* | (2006.01) |
| *C08L 53/00* | (2006.01) |

(52) U.S. Cl.
CPC .............. *C08L 51/003* (2013.01); *A61K 8/26* (2013.01); *A61K 8/8111* (2013.01); *A61K 8/8152* (2013.01); *A61K 8/8182* (2013.01); *A61K 8/891* (2013.01); *A61K 8/90* (2013.01); *A61K 8/922* (2013.01); *A61K 8/927* (2013.01); *A61Q 1/04* (2013.01); *A61Q 1/06* (2013.01); *A61Q 1/10* (2013.01); *A61Q 3/02* (2013.01); *C08F 265/04* (2013.01); *C08F 265/06* (2013.01); *C08F 291/00* (2013.01); *C08F 293/005* (2013.01); *C08L 53/00* (2013.01); *A61K 2800/594* (2013.01)

USPC ........................................................ 424/78.1

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,528,378 A | 10/1950 | Mannheimer et al. |
| 2,723,248 A | 11/1955 | Wright |
| 2,781,354 A | 2/1957 | Mannheimer et al. |
| 3,673,160 A | 6/1972 | Buisson et al. |
| 3,716,633 A | 2/1973 | Viout et al. |
| 3,802,841 A | 4/1974 | Robin |
| 3,836,537 A | 9/1974 | Boerwinkle et al. |
| 3,910,862 A | 10/1975 | Barabas et al. |
| 3,915,921 A | 10/1975 | Schlatzer et al. |
| 3,925,542 A | 12/1975 | Viout et al. |
| 3,937,811 A | 2/1976 | Papantoniou et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,030,512 A | 6/1977 | Papantoniou et al. |
| 4,031,307 A | 6/1977 | DeMartino et al. |
| 4,032,628 A | 6/1977 | Papantoniou et al. |
| 4,070,533 A | 1/1978 | Papantoniou et al. |
| 4,076,912 A | 2/1978 | Papantoniou et al. |
| RE29,871 E | 12/1978 | Papantoniou et al. |
| 4,128,631 A | 12/1978 | Lundmark et al. |
| 4,129,711 A | 12/1978 | Viout et al. |
| 4,131,576 A | 12/1978 | Iovine |
| 4,137,208 A | 1/1979 | Elliott |

(Continued)

FOREIGN PATENT DOCUMENTS

| | | |
|---|---|---|
| DE | 2 330 956 | 1/1974 |
| DE | 100 22 247 | 11/2001 |

(Continued)

OTHER PUBLICATIONS

Cortazer et al., Polymer Bulletin 1, 149-154 (1987).*

(Continued)

*Primary Examiner* — Paul Dickinson
(74) *Attorney, Agent, or Firm* — Oblon, Spivak, McClelland, Maier & Neustadt, L.L.P.

(57) ABSTRACT

The invention relates to a cosmetic composition comprising at least one non-elastomer, filmogenic, linear, sequenced, ethylenic polymer and in a cosmetically acceptable liquid medium and a gelling agent of said organic liquid medium. The invention also relates to the combination of said sequenced polymer and a gelling agent in order to improve the texture and application of said composition on keratin fibers.

95 Claims, No Drawings

(56) References Cited

U.S. PATENT DOCUMENTS

| | | | |
|---|---|---|---|
| 4,152,416 A | 5/1979 | Spitzer et al. |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |
| 4,425,326 A | 1/1984 | Guillon et al. |
| 4,509,949 A | 4/1985 | Huang et al. |
| 4,693,935 A | 9/1987 | Mazurek |
| 4,728,571 A | 3/1988 | Clemens et al. |
| 4,887,622 A | 12/1989 | Gueret |
| 4,972,037 A | 11/1990 | Garbe et al. |
| 4,981,902 A | 1/1991 | Mitra et al. |
| 4,981,903 A | 1/1991 | Garbe et al. |
| 5,000,937 A | 3/1991 | Grollier et al. |
| 5,061,481 A | 10/1991 | Suzuki et al. |
| 5,110,582 A | 5/1992 | Hungerbuhler et al. |
| 5,156,911 A | 10/1992 | Stewart |
| 5,209,924 A | 5/1993 | Garbe et al. |
| 5,219,560 A | 6/1993 | Suzuki et al. |
| 5,266,321 A | 11/1993 | Shukuzaki et al. |
| 5,362,485 A | 11/1994 | Hayama et al. |
| 5,391,631 A | 2/1995 | Porsch et al. |
| 5,468,477 A | 11/1995 | Kumar et al. |
| 5,472,798 A | 12/1995 | Kumazawa et al. |
| 5,492,426 A | 2/1996 | Gueret |
| 5,519,063 A | 5/1996 | Mondet et al. |
| 5,538,717 A | 7/1996 | De La Poterie |
| 5,681,877 A | 10/1997 | Hosotte-Filbert et al. |
| 5,686,067 A | 11/1997 | Shih et al. |
| 5,690,918 A | 11/1997 | Jacks et al. |
| 5,711,940 A | 1/1998 | Kuentz et al. |
| 5,725,882 A | 3/1998 | Kumar et al. |
| 5,736,125 A | 4/1998 | Morawsky et al. |
| 5,747,013 A | 5/1998 | Mougin et al. |
| 5,756,635 A | 5/1998 | Michaud et al. |
| 5,772,347 A | 6/1998 | Gueret |
| 5,783,657 A | 7/1998 | Pavlin et al. |
| 5,807,540 A | 9/1998 | Junino et al. |
| 5,843,407 A * | 12/1998 | El-Nokaly et al. ............ 424/64 |
| 5,849,275 A | 12/1998 | Calello et al. |
| 5,849,318 A | 12/1998 | Imai et al. |
| 5,879,095 A | 3/1999 | Gueret |
| 5,897,870 A | 4/1999 | Schehlmann et al. |
| 5,948,393 A | 9/1999 | Tomomasa et al. |
| 5,994,446 A | 11/1999 | Graulus et al. |
| 6,001,367 A | 12/1999 | Bazin et al. |
| 6,001,374 A | 12/1999 | Nichols |
| 6,027,739 A | 2/2000 | Nichols |
| 6,033,650 A | 3/2000 | Calello et al. |
| 6,059,473 A | 5/2000 | Gueret |
| 6,074,654 A | 6/2000 | Drechsler et al. |
| 6,083,516 A | 7/2000 | Curtis et al. |
| 6,106,813 A | 8/2000 | Mondet et al. |
| 6,106,820 A | 8/2000 | Morrissey et al. |
| 6,120,781 A | 9/2000 | Le Bras et al. |
| 6,126,929 A | 10/2000 | Mougin |
| 6,132,742 A | 10/2000 | Le Bras et al. |
| 6,139,849 A | 10/2000 | Lesaulnier et al. |
| 6,140,431 A | 10/2000 | Kinker et al. |
| 6,153,206 A | 11/2000 | Anton et al. |
| 6,156,804 A | 12/2000 | Chevalier et al. |
| 6,160,054 A | 12/2000 | Schwindeman et al. |
| 6,165,457 A | 12/2000 | Midha et al. |
| 6,166,093 A | 12/2000 | Mougin et al. |
| 6,174,968 B1 | 1/2001 | Hoxmeier |
| 6,180,123 B1 | 1/2001 | Mondet |
| 6,197,883 B1 | 3/2001 | Schimmel et al. |
| 6,225,390 B1 | 5/2001 | Hoxmeier |
| 6,228,946 B1 | 5/2001 | Kitayama et al. |
| 6,228,967 B1 | 5/2001 | Fost et al. |
| 6,238,679 B1 | 5/2001 | De La Poterie et al. |
| 6,254,878 B1 | 7/2001 | Bednarek et al. |
| 6,258,916 B1 | 7/2001 | Michaud et al. |
| 6,267,951 B1 | 7/2001 | Shah et al. |
| 6,268,466 B1 | 7/2001 | MacQueen et al. |
| 6,280,713 B1 | 8/2001 | Tranchant et al. |
| 6,303,105 B1 | 10/2001 | Shah et al. |
| 6,319,959 B1 | 11/2001 | Mougin et al. |
| 6,326,011 B1 | 12/2001 | Miyazawa et al. |
| 6,328,495 B1 | 12/2001 | Gueret |
| 6,342,237 B1 | 1/2002 | Bara |
| 6,372,876 B1 | 4/2002 | Kim et al. |
| 6,386,781 B1 | 5/2002 | Gueret |
| 6,395,265 B1 | 5/2002 | Mougin et al. |
| 6,399,691 B1 | 6/2002 | Melchiors et al. |
| 6,410,005 B1 | 6/2002 | Galleguillos et al. |
| 6,410,666 B1 | 6/2002 | Grubbs et al. |
| 6,412,496 B1 | 7/2002 | Gueret |
| 6,423,306 B2 | 7/2002 | Caes et al. |
| 6,464,969 B2 | 10/2002 | De La Poterie et al. |
| 6,484,731 B1 | 11/2002 | Lacout |
| 6,491,927 B1 | 12/2002 | Arnaud et al. |
| 6,518,364 B2 | 2/2003 | Charmot et al. |
| 6,531,535 B2 | 3/2003 | Melchiors et al. |
| 6,552,146 B1 | 4/2003 | Mougin |
| 6,581,610 B1 | 6/2003 | Gueret |
| 6,649,173 B1 | 11/2003 | Arnaud et al. |
| 6,663,855 B2 | 12/2003 | Frechet et al. |
| 6,663,885 B1 | 12/2003 | Hager et al. |
| 6,685,925 B2 * | 2/2004 | Frechet et al. ............ 424/70.16 |
| 6,692,173 B2 | 2/2004 | Gueret |
| 6,692,733 B1 | 2/2004 | Mougin |
| 6,770,271 B2 | 8/2004 | Mondet et al. |
| 6,805,872 B2 | 10/2004 | Mougin |
| 6,833,419 B2 | 12/2004 | Morschhauser et al. |
| 6,843,611 B2 | 1/2005 | Blondeel et al. |
| 6,866,046 B2 | 3/2005 | Gueret |
| 6,881,780 B2 | 4/2005 | Bryant et al. |
| 6,890,522 B2 | 5/2005 | Frechet et al. |
| 6,891,011 B2 | 5/2005 | Morschhauser et al. |
| 6,905,696 B2 | 6/2005 | Marotta et al. |
| 6,946,518 B2 | 9/2005 | De La Poterie |
| 6,960,339 B1 | 11/2005 | Ferrari |
| 6,964,995 B2 | 11/2005 | Morschhauser et al. |
| 7,022,791 B2 | 4/2006 | Loffler et al. |
| 7,025,973 B2 | 4/2006 | Loffler et al. |
| 7,053,146 B2 | 5/2006 | Morschhauser et al. |
| 7,081,507 B2 | 7/2006 | Morschhauser et al. |
| 7,144,171 B2 | 12/2006 | Blondeel et al. |
| 7,151,137 B2 | 12/2006 | Morschhauser et al. |
| 7,176,170 B2 | 2/2007 | Dubief et al. |
| 7,186,405 B2 | 3/2007 | Loffler et al. |
| 7,186,774 B2 | 3/2007 | Morschhauser et al. |
| 7,244,421 B2 | 7/2007 | Loffler et al. |
| 7,279,154 B2 | 10/2007 | Loffler et al. |
| 7,297,328 B2 | 11/2007 | Loffler et al. |
| 7,332,155 B2 | 2/2008 | Loffler et al. |
| 7,358,303 B2 | 4/2008 | De La Poterie |
| 7,393,520 B2 | 7/2008 | Loffler et al. |
| 7,399,478 B2 | 7/2008 | Loffler et al. |
| 7,875,265 B2 | 1/2011 | Blin et al. |
| 8,119,110 B2 | 2/2012 | Blin et al. |
| 2002/0015611 A1 | 2/2002 | Blondeel et al. |
| 2002/0018759 A1 | 2/2002 | Pagano et al. |
| 2002/0020424 A1 | 2/2002 | Gueret |
| 2002/0035237 A1 | 3/2002 | Lawson et al. |
| 2002/0054783 A1 | 5/2002 | Gueret |
| 2002/0055562 A1 | 5/2002 | Butuc |
| 2002/0061319 A1 | 5/2002 | Bernard et al. |
| 2002/0064539 A1 | 5/2002 | Philippe et al. |
| 2002/0076390 A1 | 6/2002 | Kantner et al. |
| 2002/0076425 A1 | 6/2002 | Mondet et al. |
| 2002/0098217 A1 | 7/2002 | Piot et al. |
| 2002/0115780 A1 | 8/2002 | Mougin |
| 2002/0150546 A1 | 10/2002 | Mougin et al. |
| 2002/0151638 A1 | 10/2002 | Melchiors et al. |
| 2002/0159965 A1 | 10/2002 | Frechet et al. |
| 2002/0160026 A1 | 10/2002 | Frechet et al. |
| 2003/0003154 A1 | 1/2003 | De La Poterie |
| 2003/0017124 A1 | 1/2003 | Agostini et al. |
| 2003/0017182 A1 | 1/2003 | Tournilhac |
| 2003/0021815 A9 | 1/2003 | Mondet et al. |
| 2003/0024074 A1 | 2/2003 | Hartman |
| 2003/0039621 A1 | 2/2003 | Arnaud et al. |

(56) References Cited

U.S. PATENT DOCUMENTS

| | | |
|---|---|---|
| 2003/0059392 A1 | 3/2003 | L'Alloret |
| 2003/0113285 A1 | 6/2003 | Meffert et al. |
| 2003/0124074 A1 | 7/2003 | Mougin et al. |
| 2003/0124079 A1 | 7/2003 | Mougin et al. |
| 2003/0185774 A1 | 10/2003 | Dobbs et al. |
| 2003/0191271 A1 | 10/2003 | Mondet et al. |
| 2004/0009136 A1 | 1/2004 | Dubief et al. |
| 2004/0013625 A1 | 1/2004 | Kanji |
| 2004/0014872 A1 | 1/2004 | Raether |
| 2004/0039101 A1 | 2/2004 | Dubief et al. |
| 2004/0052745 A1 | 3/2004 | Bernard et al. |
| 2004/0052752 A1 | 3/2004 | Samain et al. |
| 2004/0077788 A1 | 4/2004 | Guerra et al. |
| 2004/0091444 A1 | 5/2004 | Loffler et al. |
| 2004/0093676 A1 | 5/2004 | Vidal et al. |
| 2004/0096409 A1 | 5/2004 | Loeffler et al. |
| 2004/0096411 A1 | 5/2004 | Frechet et al. |
| 2004/0097657 A1 | 5/2004 | Morschhaeuser et al. |
| 2004/0109835 A1 | 6/2004 | Loffler et al. |
| 2004/0109836 A1 | 6/2004 | Loffler et al. |
| 2004/0109838 A1 | 6/2004 | Morschhauser et al. |
| 2004/0115148 A1 | 6/2004 | Loffler et al. |
| 2004/0115149 A1 | 6/2004 | Loffler et al. |
| 2004/0115157 A1 | 6/2004 | Loffler et al. |
| 2004/0116628 A1 | 6/2004 | Morschhauser et al. |
| 2004/0116634 A1 | 6/2004 | Morschhaeuser et al. |
| 2004/0120906 A1 | 6/2004 | Toumi et al. |
| 2004/0120920 A1 | 6/2004 | Lion et al. |
| 2004/0137020 A1 | 7/2004 | De La Poterie et al. |
| 2004/0137021 A1 | 7/2004 | De La Poterie et al. |
| 2004/0141937 A1 | 7/2004 | Loffler et al. |
| 2004/0141943 A1 | 7/2004 | Mougin et al. |
| 2004/0142831 A1 | 7/2004 | Jager Lezer |
| 2004/0167304 A1 | 8/2004 | Morschhauser et al. |
| 2004/0223933 A1 | 11/2004 | Hiwatashi et al. |
| 2004/0241118 A1 | 12/2004 | Simon et al. |
| 2005/0002724 A1 | 1/2005 | Blondeel et al. |
| 2005/0020779 A1 | 1/2005 | Mougin et al. |
| 2005/0032998 A1 | 2/2005 | Morschhaeuser et al. |
| 2005/0089536 A1 | 4/2005 | Loffler et al. |
| 2005/0095213 A1 | 5/2005 | Blin et al. |
| 2005/0106197 A1 | 5/2005 | Blin et al. |
| 2005/0129641 A1 | 6/2005 | Arnaud et al. |
| 2005/0201958 A1 | 9/2005 | De La Poterie |
| 2005/0220747 A1 | 10/2005 | Lion et al. |
| 2005/0232887 A1 | 10/2005 | Morschhauser et al. |
| 2005/0287103 A1 | 12/2005 | Filippi et al. |
| 2006/0093568 A1 | 5/2006 | Blin et al. |
| 2006/0099164 A1 | 5/2006 | De La Poterie et al. |
| 2006/0099231 A1 | 5/2006 | De La Poterie et al. |
| 2006/0115444 A1 | 6/2006 | Blin et al. |
| 2006/0127334 A1 | 6/2006 | Ferrari et al. |
| 2006/0134032 A1 | 6/2006 | Ilekti et al. |
| 2006/0134038 A1 | 6/2006 | De La Poterie et al. |
| 2006/0134044 A1 | 6/2006 | Blin et al. |
| 2006/0134051 A1 | 6/2006 | Blin et al. |
| 2006/0147402 A1 | 7/2006 | Blin et al. |
| 2006/0147403 A1 | 7/2006 | Ferrari et al. |
| 2007/0003506 A1 | 1/2007 | Mougin et al. |
| 2007/0003507 A1 | 1/2007 | Mougin et al. |
| 2007/0134181 A1 | 6/2007 | Shimizu et al. |
| 2007/0166259 A1 | 7/2007 | Vicic et al. |
| 2008/0014232 A1 | 1/2008 | Arnaud et al. |
| 2008/0025934 A1 | 1/2008 | Lebre et al. |
| 2008/0050329 A1 | 2/2008 | De La Poterie |
| 2008/0069793 A1 | 3/2008 | Loffler et al. |
| 2008/0107617 A1 | 5/2008 | Loffler et al. |
| 2008/0159965 A1 | 7/2008 | Mougin et al. |
| 2008/0207773 A1 | 8/2008 | Loffler et al. |
| 2008/0219943 A1 | 9/2008 | De La Poterie |
| 2009/0130037 A1 | 5/2009 | Thevenet et al. |
| 2010/0310489 A1 | 12/2010 | Barba |
| 2011/0020263 A1 | 1/2011 | Ilekti et al. |
| 2011/0280817 A1 | 11/2011 | Ramadan et al. |
| 2012/0171137 A1 | 7/2012 | Bradsaw et al. |
| 2012/0171139 A1 | 7/2012 | Bradshaw et al. |

FOREIGN PATENT DOCUMENTS

| | | |
|---|---|---|
| DE | 100 29 697 | 12/2001 |
| EP | 1 279 398 | 9/1971 |
| EP | 0 080 976 | 6/1983 |
| EP | 0 295 886 | 12/1988 |
| EP | 0 320 218 | 6/1989 |
| EP | 0 173 109 | 10/1989 |
| EP | 0 388 582 | 9/1990 |
| EP | 0 412 704 | 2/1991 |
| EP | 0 412 707 | 2/1991 |
| EP | 0 549 494 | 6/1993 |
| EP | 0 582 152 | 2/1994 |
| EP | 0 216 479 | 8/1994 |
| EP | 0 619 111 | 10/1994 |
| EP | 0 637 600 | 2/1995 |
| EP | 0 656 021 | 6/1995 |
| EP | 0 667 146 | 8/1995 |
| EP | 0 550 745 | 9/1995 |
| EP | 0 686 858 | 12/1995 |
| EP | 0 750 031 | 12/1996 |
| EP | 0 751 162 | 1/1997 |
| EP | 0 751 170 | 1/1997 |
| EP | 0 815 836 | 1/1998 |
| EP | 0 847 752 | 6/1998 |
| EP | 0 861 859 | 9/1998 |
| EP | 0 951 897 | 10/1999 |
| EP | 1 018 311 | 7/2000 |
| EP | 1 024 184 | 8/2000 |
| EP | 1 043 345 | 10/2000 |
| EP | 1 066 817 | 1/2001 |
| EP | 1 068 856 | 1/2001 |
| EP | 1 201 221 | 5/2002 |
| EP | 1 356 799 | 10/2003 |
| EP | 1 366 741 | 12/2003 |
| EP | 1 366 744 | 12/2003 |
| EP | 1 366 746 | 12/2003 |
| EP | 1 411 069 A2 | 4/2004 |
| EP | 1 421 928 A2 | 5/2004 |
| EP | 1 440 680 A1 | 7/2004 |
| EP | 1 518 534 | 3/2005 |
| EP | 1 518 535 | 3/2005 |
| EP | 1 604 634 | 12/2005 |
| FR | 1 222 944 | 6/1960 |
| FR | 1 400 366 | 4/1965 |
| FR | 1 564 110 | 3/1969 |
| FR | 1 580 545 | 9/1969 |
| FR | 2 077 143 | 9/1971 |
| FR | 2 079 785 | 11/1971 |
| FR | 2 140 977 | 1/1973 |
| FR | 2 232 303 | 1/1975 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 710 646 | 4/1995 |
| FR | 2 722 380 | 1/1996 |
| FR | 2 727 609 | 6/1996 |
| FR | 2 743 297 | 7/1997 |
| FR | 2 761 959 | 10/1998 |
| FR | 2 796 529 | 7/1999 |
| FR | 2 775 566 | 9/1999 |
| FR | 2 791 042 | 9/2000 |
| FR | 2 791 988 A1 | 10/2000 |
| FR | 2 792 190 | 10/2000 |
| FR | 2 792 618 | 10/2000 |
| FR | 2 798 061 | 3/2001 |
| FR | 2 806 273 | 9/2001 |
| FR | 2 809 306 | 11/2001 |
| FR | 2 811 993 | 1/2002 |
| FR | 2 814 365 | 3/2002 |
| FR | 2 816 503 | 5/2002 |
| FR | 2 823 101 | 10/2002 |

(56) References Cited

FOREIGN PATENT DOCUMENTS

| | | |
|---|---|---|
| FR | 2 823 103 | 10/2002 |
| FR | 2 827 514 A1 | 1/2003 |
| FR | 2 831 430 | 5/2003 |
| FR | 2 834 458 | 7/2003 |
| FR | 2 840 205 A1 | 12/2003 |
| FR | 2 840 209 A1 | 12/2003 |
| FR | 2 842 417 | 1/2004 |
| FR | 2 844 709 | 3/2004 |
| FR | 2 860 143 A1 | 4/2005 |
| FR | 2 860 156 A1 | 4/2005 |
| FR | 2 880 268 | 7/2006 |
| GB | 0 839 805 | 6/1960 |
| GB | 0 922 457 | 4/1963 |
| GB | 1 021 400 | 3/1966 |
| GB | 1 169 862 | 11/1969 |
| GB | 1 324 745 | 7/1973 |
| GB | 1 331 819 | 9/1973 |
| GB | 1 407 659 | 9/1975 |
| GB | 1 572 626 | 7/1980 |
| JP | 5-221829 | 8/1993 |
| JP | 06-279323 | 10/1994 |
| JP | 07-196450 | 8/1995 |
| JP | 07-309721 | 11/1995 |
| JP | 07-324017 | 12/1995 |
| JP | 08-119836 | 5/1996 |
| JP | 09-263518 | 10/1997 |
| JP | 10-506404 | 6/1998 |
| JP | H11-100307 | 4/1999 |
| JP | 11-124312 | 5/1999 |
| JP | 2000-83728 | 3/2000 |
| JP | 2000-319325 | 11/2000 |
| JP | 2000-319326 | 11/2000 |
| JP | 2001-348553 | 12/2001 |
| JP | 2001-527559 | 12/2001 |
| JP | 2002-201110 | 7/2002 |
| JP | 2002-201244 | 7/2002 |
| JP | 2003-40336 | 2/2003 |
| JP | 2003-73222 | 3/2003 |
| JP | 2003-081742 | 3/2003 |
| JP | 2003-286142 | 10/2003 |
| JP | 2004-2432 | 1/2004 |
| JP | 2004-2435 | 1/2004 |
| JP | 2004-149772 | 5/2004 |
| JP | 2004-269497 | 9/2004 |
| JP | 2005/104979 | 4/2005 |
| JP | 2006-503921 | 2/2006 |
| JP | 2006-507355 | 3/2006 |
| JP | 2006-507365 | 3/2006 |
| JP | 2006-507366 | 3/2006 |
| JP | 2006-507367 | 3/2006 |
| JP | 2006-151867 | 6/2006 |
| LU | 75370 | 7/1976 |
| LU | 75371 | 7/1976 |
| WO | WO 93/01797 | 2/1993 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 95/03776 | 2/1995 |
| WO | WO 95/06078 | 3/1995 |
| WO | WO 96/10044 | 4/1996 |
| WO | WO 97/17057 | 5/1997 |
| WO | WO 98/31329 | 7/1998 |
| WO | WO 98/38981 | 9/1998 |
| WO | WO 98/42298 | 10/1998 |
| WO | WO 98/44012 | 10/1998 |
| WO | WO 98/51276 A1 | 11/1998 |
| WO | WO 00/26285 | 5/2000 |
| WO | WO 00/28948 | 5/2000 |
| WO | WO 00/40216 | 7/2000 |
| WO | WO 00/49997 | 8/2000 |
| WO | WO 01/03538 | 1/2001 |
| WO | WO 01/13863 | 3/2001 |
| WO | WO 01/19333 | 3/2001 |
| WO | WO 01/30886 | 5/2001 |
| WO | WO 01/43703 A1 | 6/2001 |
| WO | WO 01/51018 | 7/2001 |
| WO | WO 01/89470 A1 | 11/2001 |
| WO | WO 01/95871 | 12/2001 |
| WO | WO 02/05762 | 1/2002 |
| WO | WO 02/28358 A1 | 4/2002 |
| WO | WO 02/34218 | 5/2002 |
| WO | WO 02/067877 | 9/2002 |
| WO | WO 03/018423 | 3/2003 |
| WO | WO 03/046032 | 6/2003 |
| WO | WO 03/046033 | 6/2003 |
| WO | WO 2004/022009 | 3/2004 |
| WO | WO 2004/022010 | 3/2004 |
| WO | WO 2004/024700 A1 | 3/2004 |
| WO | WO 2004/028485 A2 | 4/2004 |
| WO | WO 2004/028487 A2 | 4/2004 |
| WO | WO 2004/028491 A2 | 4/2004 |
| WO | WO 2005/030158 A1 | 4/2005 |

OTHER PUBLICATIONS

Co-pending U.S. Appl. No. 10/528,698, filed Mar. 22, 2005; Inventors: Veronique Ferrari et al.
Co-pending U.S. Appl. No. 10/528,699, filed Mar. 22, 2005; Inventors: Philippe Ilekti et al.
Co-pending U.S. Appl. No. 10/529,218, filed Mar. 25, 2005; Inventors: Xavier Blin et al.
Co-pending U.S. Appl. No. 10/529,264, filed Mar. 25, 2005; Inventors: Veronique Ferrari et al.
Co-pending U.S. Appl. No. 10/529,266, filed Mar. 25, 2005; Inventors: Xavier Blin et al.
Co-pending U.S. Appl. No. 10/529,318, filed Mar. 25, 2005; Inventors: Xavier Blin et al.
English Derwent Abstract for EP 1 082 953.
English Derwent Abstract for EP 1 159 950.
English Derwent Abstract for FR 2 832 719.
English Derwent Abstract for FR 2 803 743.
English Derwent Abstract for WO 04/028489.
International Search Report for PCT/FR03/002844 (Priority Application for U.S. Appl. No. 10/529,318), dated May 14, 2005.
International Search Report for PCT/FR03/002847 (Priority Application for U.S. Appl. No. 10/529,266), dated May 17, 2004.
International Search Report for PCT/FR03/02842 (Priority Application for U.S. Appl. No. 10/529,218), dated May 17, 2004.
International Search Report for PCT/FR03/02843 (Priority Application for U.S. Appl. No. 10/528,698), dated May 17, 2004.
International Search Report for PCT/FR03/02845 (Priority Application for U.S. Appl. No. 10/529,264), dated May 17, 2004.
International Search Report for PCT/FR03/02846 (Priority Application for U.S. Appl. No. 10/528,699), dated May 17, 2004.
International Search Report for PCT/FR03/02848 (Priority Application for U.S. App. No. 10/528,835), dated May 17, 2004.
English language Derwent Abstract for FR 2 775 566.
English language Derwent Abstract for FR 2 798 061.
Aldrich: Polymer Properties; 4th Ed. Catalog No. Z41, 247-3 (1999) published by John Wiley, New York.
Boutevin, B. et al., "Study of Morphological and Mechanical Properties of PP/PBT," Polymer Bulletin, 34, pp. 117-123, (1995).
Buzin, A. et al., "Calorimetric Study of Block-Copolymers of Poly(n-butyl Acrylate) and Gradient Poly(n-butyl acrylate-co-methyl methacrylate)" vol. 43, 2002, pp. 5563-5569.
Co-pending U.S. Appl. No. 10/529,265, filed Sep. 28, 2005; Inventors: Xavier Blin et al.
Co-pending U.S. Appl. No. 10/529,267, filed Sep. 29, 2005; Inventors: Valerie De La Poterie et al.
Co-pending U.S. Appl. No. 10/573,579; filed Dec. 26, 2006; Inventor: Marco Vicic et al.
Co-pending U.S. Appl. No. 10/585,817, filed Jan. 10, 2007; Inventor: Valerie De La Poterie.
Co-pending U.S. Appl. No. 10/585,818, filed Jul. 12, 2006; Inventors: Valerie De La Poterie.
Co-pending U.S. Appl. No. 10/670,388, filed Sep. 26, 2003; Inventors: Beatrice Toumi et al.

(56) References Cited

OTHER PUBLICATIONS

Co-pending U.S. Appl. No. 10/670,478, filed Sep. 26, 2003; Inventors: Bertrand Lion et al.
Co-pending U.S. Appl. No. 10/949,448, filed Sep. 27, 2004; Inventors: Xavier Blin et al.
Co-pending U.S. Appl. No. 11/086,906, filed Mar. 23, 2005; Inventors: Philippe Ilekti et al.
Co-pending U.S. Appl. No. 11/089,210, filed Mar. 25, 2005.
Co-pending U.S. Appl. No. 11/858,994, filed Sep. 21, 2007; Inventors: Bertrand Lion et al.
Co-pending U.S. Appl. No. 11/859,004, filed Sep. 21, 2007; Inventors: Bertrand Lion et al.
Co-pending U.S. Appl. No. 11/859,015, filed Sep. 21, 2007; Inventors: Bertrand Lion et al.
English language Abstract of FR 2 710 552, dated Apr. 7, 1995.
English language Abstract of FR 2 710 646, dated Apr. 7, 1995.
English language Abstract of FR 2 791 987, dated Oct. 13, 2000.
English language Abstract of FR 2 832 720, dated May 30, 2003.
English language Abstract of FR 2 834 458, dated Jul. 11, 2003.
English language Abstract of JP 07-309721, dated Nov. 28, 1995.
English language Abstract of JP 08-119836, dated May 14, 1996.
English language Abstract of WO 01/13863, dated Mar. 1, 2001.
English language Abstract of WO 01/51018, dated Jul. 19, 2001.
English language Derwent Abstract for EP 0 080 976, dated Jun. 8, 1983.
English language Derwent Abstract for EP 0 815 836, dated Jan. 7, 1998.
English language Derwent Abstract for FR 2 775 566, dated Sep. 10, 1999.
English language Derwent Abstract for FR 2 792 190, dated Oct. 20, 2000.
English language Derwent Abstract for FR 2 831 430, dated May 2, 2003.
English language Derwent Abstract for JP 06-279323, dated Oct. 4, 1994.
English language Derwent Abstract for JP 07-196450, dated Aug. 1, 1995.
English language Derwent Abstract for JP 09-263518, dated Oct. 7, 1997.
English language Derwent Abstract for JP 11-124312, dated May 11, 1999.
English language Derwent Abstract of DE 100 29 697, dated Dec. 20, 2001.
English language Derwent Abstract of EP 0 648 485, dated Apr. 19, 1995.
English language Derwent Abstract of FR 2 140 977, dated Jan. 19, 1973.
English language Derwent Abstract of JP 2002-201244, dated Jul. 19, 2002.
English language Derwent Abstract of JP 5-221829, dated Aug. 31, 1993.
European Search Report for EP 03 292 383, dated May 17, 2004, in Co-pending U.S. Appl. No. 10/670,388.
Flick, "Cosmetic Additives: An Industrial Guide", Noyes Publications, Park Ridge, NJ, p. 266 (1991).
Fonnum, et al., Colloid Polym. Sci., 1993, 271: 380-389.
French Search Report for FR 02/11949 for Copending U.S. Appl. No. 10/670,478, dated Jul. 7, 2003.
French Search Report for FR 03/11340 for Copending U.S. Appl. No. 10/949,448, dated May 9, 2005.
French Search Report for FR 04/03090, dated Sep. 30, 2004, (Priority document for Copending U.S. Appl. No. 11/089,210).
French Search Report for FR 04/50572, for Copending U.S. Appl. No. 11/086,906, dated Nov. 9, 2004.
Hamley, I.W., "Crystallization in Block Copolymers," Advances in Polymer Science, vol. 148, pp. 113-137 (1999).
Hansen, C.M., "The Three Dimensional Solubility Parameter—Key to Paint Component Affinities: I. Solvents, Plasticizers, Polymers, and Resins", Journal of Paint Technology, vol. 39, No. 505, pp. 104-117 (1967).
HCAPLUS abstract 1964: 70247, abstracting: Develop. Ind. Microbiol., vol. 2, pp. 47-53 (1961).
International Search Report for PCT Application No. PCT/FR03/02849, dated Jun. 24, 2004.
International Search Report for PCT/FR03/02841, dated Jun. 1, 2004.
International Search Report for PCT/IB2005/000230, dated May 27, 2005, (PCT counterpart to Co-pending U.S. Appl. No. 10/585,817).
International Search Report for PCT/IB2005/000236, dated Aug. 3, 2005, (PCT counterpart to Co-pending U.S. Appl. No. 10/585,818).
Kirk-Othmer, "Encyclopedia of Chemical Technology", vol. 22, 3rd Edition, Wiley, 1979, pp. 333-432.
Nojima. S., "Melting Behavior of Poly (E-caprolactone)-block-polybutadiene Copolymers", Macromolecules, 32, 3727-3734 (1999).
Office Action mailed Aug. 12, 2005, in co-pending U.S. Appl. No. 10/670,478.
Office Action mailed Aug. 12, 2009 in co-pending U.S. Appl. No. 10/949,448.
Office Action mailed Aug. 18, 2009 in co-pending U.S. Appl. No. 10/529,264.
Office Action mailed Dec. 10, 2008, in co-pending U.S. Appl. No. 10/528,698.
Office Action mailed Dec. 23, 2008, in co-pending U.S. Appl. No. 10/529,266.
Office Action mailed Jan. 7, 2008, in co-pending U.S. Appl. No. 10/670,388.
Office Action mailed Jun. 12, 2009 in co-pending U.S. Appl. No. 11/086,906.
Office Action mailed Jun. 24, 2009 in co-pending U.S. Appl. No. 10/528,698.
Office Action mailed Jun. 24, 2009 in co-pending U.S. Appl. No. 10/529,267.
Office Action mailed Jun. 29, 2009 in co-pending U.S. Appl. No. 10/529,266.
Office Action mailed Jun. 4, 2009 in co-pending U.S. Appl. No. 10/670,478.
Office Action mailed Jun. 8, 2009 in co-pending U.S. Appl. No. 11/089,210.
Office Action mailed Mar. 12, 2009, in co-pending U.S. Appl. No. 10/529,218.
Office Action mailed Mar. 18, 2009, in co-pending U.S. Appl. No. 10/528,699.
Office Action mailed Mar. 18, 2009, in co-pending U.S. Appl. No. 10/573,579.
Office Action mailed Mar. 26, 2008, in co-pending U.S. Appl. No. 10/670,478.
Office Action mailed Mar. 7, 2006, in co-pending U.S. Appl. No. 10/670,478.
Office Action mailed May 3, 2007, in co-pending U.S. Appl. No. 10/670,478.
Office Action mailed Nov. 15, 2006, in co-pending U.S. Appl. No. 10/670,478.
Office Action mailed Nov. 25, 2008, in co-pending U.S. Appl. No. 10/949,448.
Office Action mailed Nov. 25, 2008, in co-pending U.S. Appl. No. 10/670,388.
Office Action mailed Oct. 1, 2008, in co-pending U.S. Appl. No. 10/529,318.
Office Action mailed Oct. 21, 2008, in co-pending U.S. Appl. No. 10/670,478.
Office Action mailed Sep. 2, 2009 in co-pending U.S. Appl. No. 10/529,318.
Office Action mailed Sep. 7, 2007, in co-pending U.S. Appl. No. 10/670,478.
Pigeon, R. et al., Chimie Macromoleculaire Appliquee, No. 600, 40/41 (1074), pp. 139-158.
Porter, "Chapter 7: Non Ionics," Handbook of Surfactants, 1991, pp. 116-178, Chapman and Hall, New York.
Prince, L.M. ed., Macroemulsions Theory and Practice, Academic Press (1977), pp. 21-32.

(56) References Cited

OTHER PUBLICATIONS

Rangarajan P., et al., "Morphology of Semi-Crystalline Block Copolymers of Ethylene-(ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
Thermal_Transisitons_of_Homopolymers.pdf. Thermal Transistions of Homopolymers: Glass Transistion & Melting Point Data. Accessed online Dec. 19, 2008 at: http://www.sigmaaldrich.com/etc/medialib/docs/Aldrich/General_Information/thermal_transitions_of_homopolymers.Par.0001.File.tmp/thermal_transitions_of_homopolymers.pdf.
Co-pending U.S. Appl. No. 11/878,067, filed Jul. 20, 2007; Inventors: Caroline Lebre et al.
Co-pending U.S. Appl. No. 11/878,849, filed Jul. 27, 2007; Inventors: Celine Farcet et al.
English language Abstract of EP 1 604 634, dated Dec. 14, 2005.
English language Abstract of FR 2 357 241, dated Feb. 3, 1978.
English language Abstract of FR 2 880 268, dated Jul. 7, 2006.
English language Abstract of JP 2006-151867, dated Jun. 15, 2006.
French Search Report for FR 04/03088, dated Nov. 2, 2004.
French Search Report for FR 06/53144, dated Feb. 13, 2007.
French Search Report for FR 06/53154, dated Apr. 2, 2007.
Specific Gravity and Viscosity of Liquid Table; available at http://www.csgnetwork.com/sgvisc.html. Sesame seed oil information originally published Mar. 28, 2002.
Toniu et al., "Process for Preparation of Block Polymers, Products Obtained by Means of the Process and Cosmetic Compositions Containing Them", 1973, French Patent Office, pp. 1-26 (English translation of French Patent No. FR2140977).
Notice of Allowance in U.S. Appl. No. 10/670,478 dated Jul. 6, 2010.
Office Action mailed Aug. 2, 2010, in co-pending U.S. Appl. No. 10/949,435.
Office Action mailed Aug. 31, 2010, in co-pending U.S. Appl. No. 10/529,265.
Office Action mailed Feb. 2, 2010, in co-pending U.S. Appl. No. 10/949,448.
Office Action mailed Feb. 27, 2009, in co-pending U.S. Appl. No. 11/878,849.
Office Action mailed Jan. 28, 2010, in co-pending U.S. Appl. No. 10/529,264.
Office Action mailed Jul. 12, 2010, in co-pending U.S. Appl. No. 11/858,994.
Office Action mailed Jul. 21, 2009, in co-pending U.S. Appl. No. 11/878,067.
Office Action mailed Jul. 28, 2010, in co-pending U.S. Appl. No. 10/529,264.
Office Action mailed Jul. 9, 2010, in co-pending U.S. Appl. No. 11/859,004.
Office Action mailed Jul. 9, 2010, in co-pending U.S. Appl. No. 11/859,015.
Office Action mailed Mar. 17, 2010, in co-pending U.S. Appl. No. 10/529,318.
Office Action mailed Mar. 18, 2009, in related U.S. Appl. No. 11/089,172.
Office Action mailed Mar. 30, 2010, in co-pending U.S. Appl. No. 11/089,210.
Office Action mailed Mar. 30, 2010, in co-pending U.S. Appl. No. 11/878,067.
Office Action mailed May 12, 2010, in co-pending U.S. Appl. No. 11/086,906.
Office Action mailed May 28, 2010, in co-pending U.S. Appl. No. 10/573,579.
Office Action mailed Sep. 9, 2009, in co-pending U.S. Appl. No. 11/878,849.
Related U.S. Appl. No. 11/089,172, filed Mar. 25, 2005, Inventors: Katarina Benabdillah et al.
U.S. Appl. No. 14/354,719, filed Apr. 28, 2014, Bukawa, et al.
U.S. Appl. No. 14/359,791, filed May 21, 2014, Bui, et al.
U.S. Appl. No. 14/363,215, filed Jun. 5, 2014, Bukawa, et al.
Derwent Abstract of FR 2 860 156.
Derwent Abstract of JP 2001/348553.
Derwent Abstract of JP H11-100307.
Derwent Abstract of JP 2004/002435.
Derwent Abstract of JP 2004/002432.
International Search Report for PCT/FRO3/02848 (Priority Application for U.S. App. No. 10/528,835), dated May 17, 2004, Ex. Loiselet-Taisne.
Co-pending U.S. Appl. No. 10/949,435, filed Sep. 27, 2004; Inventors: Xavier Blin et al.
English language Abstract of JP 2003-40336, Feb. 13, 2003.
Erichsen et al., "Molecular Weight Dependence of the Surface Glass Transition of Polystyrene Films Investigated by the Embedding of Gold Nanoclusters," *MRS Publication*, 2001.
Nojiri et al., "Molecular Weight Dependence of the Glass Transition Temperature in Poly(vinyl acetate)," *Japan J. Appl. Phys.*, 10 (1971), p. 803.
U.S. Appl. No. 13/729,631, filed Dec. 28, 2012, Kawaratani, et al.

\* cited by examiner

COMPOSITION COMPRISING AT LEAST ONE BLOCK POLYMER AND AT LEAST ONE GELLING AGENT

This application is a national stage application from International Application No. PCT/FR2003/002848, filed Sep. 26, 2003, which claims priority to French Application No. FR 02/11949, filed on Sep. 26, 2002; French Application No. FR 02/16437, filed on Dec. 20, 2002; and French Application No. FR 03/06121, filed on May 21, 2003, the contents of all of which are herein incorporated by reference.

The present invention relates to a cosmetic composition for making up or caring for human bodily and facial skin, the scalp included, the lips or epidermal derivatives of human beings, such as the hair, eyebrows, eyelashes or nails, which comprises a particular block polymer.

The composition may be a loose or compact powder, a foundation, a rouge, an eyeshadow, a concealer, a blusher, a lipstick, a lip balm, a lipgloss, a lip pencil, an eye pencil, a mascara, an eyeliner, a nail varnish or even a body makeup product or a skin colouring product.

Known compositions exhibit poor staying power over time, particularly as regards the colour. This poor staying power is characterized by an alteration in colour (colour change, fading), generally as a result of interaction with the sebum and/or perspiration secreted by the skin, in the case of foundation and of rouge or eyeshadow, or of interaction with the saliva, in the case of lipsticks. This alteration obliges the user to apply fresh makeup at frequent intervals, which may constitute a loss of time.

So-called "non-transfer" makeup compositions for the lips and skin are compositions which have the advantage of forming a deposit which at least in part is not deposited on the supports with which they are brought into contact (glass, clothing, cigarette, fabrics).

Known non-transfer compositions are generally based on silicone resins and volatile silicone oils and, although exhibiting improved staying properties, have the drawback of leaving on the skin and lips, following evaporation of the volatile silicone oils, a film which over time becomes uncomfortable (giving sensations of drying and tightening), thereby distancing a certain number of women from this type of lipstick.

Known non-transfer compositions contain volatile oils in association with film-forming polymers, which may be soluble in the oils, so as to limit the transfer of colour. The introduction of these polymers in solution in volatile solvents, however, has the disadvantage of leading to formulas which are sometimes of low viscosity, owing in particular to the use of oil of very low viscosity and, in particular, of volatile oils. This low rheology goes hand in hand with awkward and unattractive application, with the added factor that the drying due to the presence of the volatiles may fix these inhomogeneities of deposition.

There continues to be a need for a cosmetic product which should at one and the same time be a non-transfer product with good staying power and good texture which is easy to apply and leads to a homogeneous deposit.

The composition of the invention may in particular constitute a product for making up the body, the lips or the epidermal derivatives of human beings which has, in particular, non-therapeutic treatment and/or care properties. It constitutes in particular a lipstick or a lipgloss, a rouge or eyeshadow, a tattooing product, a mascara, an eyeliner, a nail varnish, an artificial skin-tanning product or a hair colouring or haircare product.

Surprisingly the inventors have found that a composition comprising a cosmetically acceptable organic liquid medium, at least one particular block polymer and a gelling agent for the said medium exhibits good spreading and lubricity properties and allows a homogeneous makeup result to be obtained. Moreover, the composition is glossy, does not transfer and has good staying power.

More specifically the invention provides first a cosmetic composition comprising, in a cosmetically acceptable organic liquid medium, at least one non-elastomeric film-forming ethylenic linear block polymer and a gelling agent for the said organic liquid medium.

The present invention likewise provides a cosmetic composition comprising, in a cosmetically acceptable organic liquid medium, at least one film-forming ethylenic linear block polymer free from styrene units, and a gelling agent for the said organic liquid medium.

The invention also relates to a method of making up the skin and/or the lips and/or the epidermal derivatives which consists in applying to the skin and/or the lips and/or the epidermal derivatives the composition as defined above.

The composition according to the invention may be applied to the skin of the face, the scalp and the body, the mucosae such as the lips, the inside of the lower eyelids, and the epidermal derivatives such as the nails, eyebrows, hair, eyelashes, and even body hair.

Preferably the composition according to the invention is not a rinse-off composition.

The invention likewise relates to the cosmetic use of the composition defined above for enhancing the homogeneity of makeup on the skin and/or the lips and/or the epidermal derivatives.

The invention provides finally for the use of a gelling agent in a composition comprising a block polymer as described above for the purpose of obtaining a composition which has good texture, is easy to apply and leads to a deposit which is glossy, does not migrate and/or has good staying power and/or is homogeneous.

Block Polymer:

The composition according to the present invention comprises at least one block polymer. By "block" polymer is meant a polymer comprising at least 2 distinct blocks, preferably at least 3 distinct blocks.

According to one embodiment the block polymer of the composition according to the invention is an ethylenic polymer. By "ethylenic" polymer is meant a polymer obtained by polymerizing monomers comprising an ethylenic unsaturation.

According to one embodiment the block polymer of the composition according to the invention is a linear polymer. By opposition, a polymer having a non-linear structure is, for example, a polymer having a branched, starburst, graft or other structure.

According to one embodiment the block polymer of the composition according to the invention is a film-forming polymer. By "film-forming" polymer is meant a polymer capable of forming, by itself or in the presence of an auxiliary film-forming agent, a continuous and adherent film on a support, particularly on keratin materials.

According to one embodiment the block polymer of the composition according to the invention is a non-elastomeric polymer.

By "non-elastomeric polymer" is meant a polymer which, when subjected to a stress intended to stretch it (for example by 30% relative to its initial length), does not return to a length substantially identical to its initial length when the stress ceases.

More specifically the term "non-elastomeric polymer" denotes a polymer having an instantaneous recovery $R_i$<50% and a retarded recovery $R_{2h}<70\%$ after having undergone 30% elongation. Preferably $R_i$ is <30% and $R_{2h}$ is <50%.

More specifically the non-elastomeric character of the polymer is determined in accordance with the following protocol:

A polymer film is prepared by pouring a solution of the polymer into a Teflon-coated mould and then drying it for 7 days in an environment controlled at 23±5° C. and 50±10% relative humidity.

This gives a film approximately 100 μm thick, from which rectangular specimens are cut (using a punch, for example) 15 mm wide and 80 mm long.

This sample is subjected to a tensile stress by means of an apparatus sold under the reference Zwick, under the same temperature and humidity conditions as for drying.

The specimens are stretched at a speed of 50 mm/min, and the distance between the jaws is 50 mm, corresponding to the initial length ($l_0$) of the specimen.

The instantaneous recovery Ri is determined as follows:
the specimen is stretched by 30% ($\epsilon_{max}$), i.e. about 0.3 times its initial length ($l_0$);
the stress is released by applying a return speed equal to the tensile speed, i.e. 50 mm/min, and the residual elongation of the specimen is measured as a percentage, after return to zero stress ($\epsilon_i$).

The instantaneous recovery in % ($R_i$) is given by the formula below:

$$R_i=(\epsilon_{max}-\epsilon_i)/\epsilon_{max})\times 100$$

To determine the retarded recovery the residual elongation of the specimen is measured as a percentage ($\epsilon_{2h}$) 2 hours after return to zero stress.

The retarded recovery in % ($R_{2h}$) is given by the formula below:

$$R_{2h}=(\epsilon_{max}-\epsilon_{2h})/\epsilon_{max})\times 100$$

Purely by way of indication, a polymer according to one embodiment of the invention possesses an instantaneous recovery $R_i$ of 10% and a retarded recovery $R_{2h}$ of 30%.

According to another embodiment the block polymer of the composition according to the invention does not include a styrene unit. By polymer free from styrene units is meant a polymer containing less than 10%, preferably less than 5%, preferably less than 2%, more preferably less than 1% by weight i) of styrene unit of formula —CH($C_6H_5$)—$CH_2$— or ii) of substituted styrene unit, for example methylstyrene, chlorostyrene or chloromethylstyrene.

According to one embodiment the block polymer of the composition according to the invention is obtained from aliphatic ethylenic monomers. By aliphatic monomer is meant a monomer containing no aromatic group.

According to one embodiment the block polymer is an ethylenic polymer obtained from aliphatic ethylenic monomers comprising a carbon-carbon double bond and at least one ester group —COO— or amide group —CON—. The ester group may be bonded to one of the two unsaturated carbons via the carbon atom or the oxygen atom. The amide group may be bonded to one of the two unsaturated carbons via the carbon atom or the nitrogen atom.

According to one mode of implementation the block polymer comprises at least one first block and at least one second block.

By "at least" one block is meant one or more blocks.

It is specified that, in the text above and below, the terms "first" and "second" blocks in no way condition the order of the said blocks (or sequences) in the structure of the polymer.

According to one mode of implementation the block polymer comprises at least one first block and at least one second block which have different glass transition temperatures (Tgs).

In this mode of implementation the first and second blocks may be connected to one another by an intermediate segment having a glass transition temperature between the glass transition temperatures of the first and second blocks.

According to one mode of implementation the block polymer comprises at least one first block and at least one second block connected to one another by an intermediate segment comprising at least one constituent monomer of the first block and at least one constituent monomer of the second block.

Preferably the intermediate block is obtained essentially from constituent monomers of the first block and of the second block.

By "essentially" is meant to an extent of at least 85%, preferably at least 90%, more preferably 95% and more preferably still 100%.

Advantageously the intermediate segment comprising at least one constituent monomer of the first block and at least one constituent monomer of the second block of the polymer is a random polymer.

According to one mode of implementation the block polymer comprises at least one first block and at least one second block which are incompatible in the organic liquid medium of the composition of the invention.

By "blocks incompatible with one another" is meant that the mixture formed from the polymer corresponding to the first block and from the polymer corresponding to the second block is not miscible in the liquid that is in a majority by weight in the organic liquid medium of the composition, at ambient temperature (25° C.) and atmospheric pressure ($10^5$ Pa), for a polymers mixture content greater than or equal to 5% by weight, relative to the total weight of the mixture (polymers and majority organic liquid), with the provisos that i) the said polymers are present in the mixture in an amount such that the respective weight ratio ranges from 10/90 to 90/10, and that ii) each of the polymers corresponding to the first and second blocks has an average molecular mass (by weight or by number) equal to that of the block polymer+/−15%.

In the case where the organic liquid medium comprises a mixture of organic liquids, should two or more liquids be present in identical mass proportions, the said polymers mixture is not miscible in at least one of them.

In the case where the organic liquid medium comprises a single organic liquid, the said liquid, quite obviously, constitutes the liquid that is in a majority by weight.

By "organic liquid medium" is meant a medium comprising at least one organic liquid, in other words at least one organic compound which is liquid at ambient temperature (25° C.) and atmospheric pressure ($10^5$ Pa). According to one mode of implementation the majority liquid of the organic liquid medium is a volatile or non-volatile oil (fat). Preferably the organic liquid is cosmetically acceptable (acceptable tolerance, toxicology and feel). The organic liquid medium is cosmetically acceptable in the sense that it is compatible with keratin materials, such as the oils or organic solvents commonly employed in cosmetic compositions.

According to one mode of implementation the majority liquid of the organic liquid medium is the polymerization solvent or one of the polymerization solvents of the block polymer, as are described below.

By polymerization solvent is meant a solvent or a mixture of solvents. The polymerization solvent may be selected in particular from ethyl acetate, butyl acetate, alcohols such as isopropanol and ethanol, aliphatic alkanes such as isododecane, and mixtures thereof. Preferably the polymerization solvent is a mixture of butyl acetate and isopropanol, or isododecane.

Generally speaking, the block polymer may be incorporated into the composition at a high solids content, typically more than 10%, more than 20% and more preferably more than 30% and more preferably still more than 45% by weight relative to the total weight of the composition, while being easy to formulate.

Preferentially the block polymer does not include silicon atoms in its skeleton. By "skeleton" is meant the main chain of the polymer, as opposed to the pendent side chains.

Preferably the polymer according to the invention is not water-soluble, which is to say that the polymer is not soluble in water or in a mixture of water and linear or branched lower monoalcohols having 2 to 5 carbon atoms, such as ethanol, isopropanol or n-propanol, without a change in pH, at an active substance content of at least 1% by weight, at ambient temperature (25° C.).

According to one mode of implementation the block polymer has a polydispersity index I of greater than 2.

Advantageously the block polymer used in the compositions according to the invention has a polydispersity index I of greater than 2, ranging for example from 2 to 9, preferably greater than or equal to 2.5, ranging for example from 2.5 to 8, and better still greater than or equal to 2.8, and in particular ranging from 2.8 to 6.

The polydispersity index I of the polymer is equal to the ratio of the weight-average mass Mw to the number-average mass Mn.

The weight-average (Mw) and number-average (Mn) molar masses are determined by liquid chromatography by gel permeation (THF solvent, calibration curve established with standards of linear polystyrene, refractometric detector).

The weight-average mass (Mw) of the block polymer is preferably less than or equal to 300 000, and ranges for example from 35 000 to 200 000, better still from 45 000 to 150 000.

The number-average mass (Mn) of the block polymer is preferably less than or equal to 70 000, and ranges for example from 10 000 to 60 000, better still from 12 000 to 50 000.

Each block or sequence of the block polymer is obtained from one type of monomer or from two or more different types of monomers.

This signifies that each block may be composed of a homopolymer or of a copolymer; this copolymer, constituting the block, may in turn be random or alternating.

The glass transition temperatures indicated for the first and second blocks may be theoretical Tgs determined from the theoretical Tgs of the constituent monomers of each of the blocks, which can be found in a reference manual such as the Polymer Handbook, 3rd ed., 1989, John Wiley, according to the following relationship, called Fox's Law:

$$1/Tg = \Sigma(\omega_i/Tg_i)$$

$$\frac{1}{Tg} = \sum_i \frac{\omega_i}{Tg_i}$$

$\omega$ i being the mass fraction of the monomer i in the block in question and $Tg_i$ being the glass transition temperature of the homopolymer of the monomer i.

Unless indicated otherwise, the Tgs indicated for the first and second blocks in the present specification are theoretical Tgs.

The difference between the glass transition temperatures of the first and second blocks is generally greater than 10° C., preferably greater than 20° C. and more preferably greater than 30° C.

In particular the block polymer comprises at least one first block and at least one second block such that the first block may be selected from:
 a) a block with a Tg of greater than or equal to 40° C.,
 b) a block with a Tg of less than or 25 equal to 20° C.,
 c) a block with a Tg of between 20 and 40° C., and the second block may be selected from a category a), b) or c) different from the first block.

In the present invention, the expression "between . . . and . . . " is intended to denote a range of values for which the limits mentioned are excluded, and the expression "from . . . to . . . " and "ranging from . . . to . . . " is intended to denote a range of values for which the limits are included.

a) Block with a Tg of Greater than or Equal to 40° C.

The block with a Tg of greater than or equal to 40° C. has, for example, a Tg ranging from 40 to 150° C., preferably greater than or equal to 50° C., ranging for example from 50° C. to 120° C., and better still greater than or equal to 60° C., ranging for example from 60° C. to 120° C.

The block with a Tg of greater than or equal to 40° C. may be a homopolymer or a copolymer.

The block with a Tg of greater than or equal to 40° C. may be obtained totally or partly from one or more monomers which are such that the homopolymer prepared from these monomers has a glass transition temperature of greater than or equal to 40° C.

In the case where this block is a homopolymer, it is obtained from monomers which are such that the homopolymers prepared from these monomers have glass transition temperatures of greater than or equal to 40° C. This first block may be a homopolymer composed of a single type of monomer (for which the Tg of the corresponding homopolymer is greater than or equal to 40° C.).

In the case where the first block is a copolymer, it may be obtained totally or partly from one or more monomers, the nature and concentration of which are selected such that the Tg of the resulting copolymer is greater than or equal to 40° C. The copolymer may comprise, for example:
 monomers which are such that the homopolymers prepared from these monomers have Tgs of greater than or equal to 40° C., for example a Tg ranging from 40 to 150° C., preferably greater than or equal to 50° C., ranging for example from 50° C. to 120° C., and better still greater than or equal to 60° C., ranging for example from 60° C. to 120° C., and
 monomers which are such that the homopolymers prepared from these monomers have Tgs of less than 40° C., selected from monomers with a Tg of between 20 to 40° C. and/or monomers with a Tg of less than or equal to 20° C., for example a Tg ranging from −100 to 20° C., preferably less than 15° C., especially ranging from −80° C. to 15° C. and better still less than 10° C., for example ranging from −50° C. to 0° C., as described later.

The monomers whose homopolymers have a glass transition temperature of greater than or equal to 40° C. are selected, preferably, from the following monomers, also known as principal monomers:
 methacrylates of formula $CH_2=C(CH_3)-COOR_1$, in which $R_1$ represents a linear or branched unsubstituted alkyl group containing from 1 to 4 carbon atoms, such as a methyl, ethyl, propyl or isobutyl group, or $R_1$ represents a $C_4$ to $C_{12}$ cycloalkyl group;

acrylates of formula $CH_2=CH-COOR_2$ in which $R_2$ represents a $C_4$ to $C_{12}$ cycloalkyl group, such as isobornyl acrylate or a tert-butyl group;

(meth)acrylamides of formula:

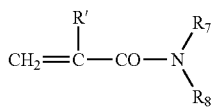

where $R_7$ and $R_8$, which are identical or different, each represent a hydrogen atom or a linear or branched $C_1$ to $C_{12}$ alkyl group, such as an n-butyl, t-butyl, isopropyl, isohexyl, isooctyl or isononyl group; or $R_7$ represents H and $R_8$ represents a 1,1-dimethyl-3-oxobutyl group and R' denotes H or methyl. Examples of monomers that may be mentioned include N-butylacrylamide, N-t-butylacrylamide, N-isopropylacrylamide, N,N-dimethylacrylamide and N,N-dibutylacrylamide;

and mixtures thereof.

Principal monomers that are particularly preferred are methyl methacrylate, isobutyl (meth)acrylate and isobornyl (meth)acrylate, and mixtures thereof.

b) Block with a Tg of Less than or Equal to 20° C.

The block with a Tg of less than or equal to 20° C. has, for example, a Tg ranging from −100 to 20° C., preferably less than or equal to 15° C., especially ranging from −80° C. to 15° C. and better still less than or equal to 10° C., for example ranging from −50° C. to 0° C.

The block with a Tg of less than or equal to 20° C. may be a homopolymer or a copolymer.

The block with a Tg of less than or equal to 20° C. may be obtained totally or partly from one or more monomers which are such that the homopolymer prepared from these monomers has a glass transition temperature of less than or equal to 20° C.

In the case where this block is a homopolymer, it is obtained from monomers which are such that the homopolymers prepared from these monomers have glass transition temperatures of less than or equal to 20° C. This second block may be a homopolymer composed of a single type of monomer (for which the Tg of the corresponding homopolymer is less than or equal to 20° C.)

In the case where the block with a Tg of less than or equal to 20° C. is a copolymer, it may be obtained totally or partly from one or more monomers, the nature and concentration of which are selected such that the Tg of the resulting copolymer is less than or equal to 20° C.

It may comprise, for example
one or more monomers whose corresponding homopolymer has a Tg of less than or equal to 20° C., for example a Tg ranging from −100° C. to 20° C., preferably less than 15° C., especially ranging from −80° C. to 15° C. and better still less than 10° C., for example ranging from −50° C. to 0° C., and
one or more monomers whose corresponding homopolymer has a Tg of greater than 20° C., such as monomers with a Tg of greater than or equal to 40° C., for example a Tg ranging from 40 to 150° C., preferably greater or equal to 50° C., ranging for example from 50° C. to 120° C. and better still greater than or equal to 60° C., ranging for example from 60° C. to 120° C. and/or monomers with a Tg of between 20 and 40° C., as described above.

Preferably the block with a Tg of less than or equal to 20° C. is a homopolymer.

The monomers whose homopolymer has a Tg of less than or equal to 20° C. are selected, preferably, from the following monomers, or principal monomer:
acrylates of formula $CH_2=CHCOOR_3$, $R_3$ representing a linear or branched $C_1$ to $C_{12}$ unsubstituted alkyl group, with the exception of the tert-butyl group, in which one or more heteroatoms selected from O, N and S is (are) optionally intercalated;
methacrylates of formula $CH_2=C(CH_3)-COOR_4$, $R_4$ representing a linear or branched $C_6$ to $C_{12}$ unsubstituted alkyl group, in which one or more hetero-atoms selected from O, N and S is (are) optionally intercalated;
vinyl esters of formula $R_5-CO-O-CH=CH_2$ where $R_5$ represents a linear or branched $C_4$ to $C_{12}$ alkyl group;
$C_4$ to $C_{12}$ alkyl vinyl ethers;
N—($C_4$ to $C_{12}$ alkyl)acrylamides, such as N-octylacrylamide;
and mixtures thereof.

The principal monomers that are particularly preferred for the block with a Tg of less than or equal to 20° C. are alkyl acrylates in which the alkyl chain contains from 1 to 10 carbon atoms, with the exception of the tert-butyl group, such as methyl acrylate, isobutyl acrylate and 2-ethylhexyl acrylate, and mixtures thereof.

c) Block with a Tg of between 20 and 40° C.

The block which has a Tg of between 20 and 40° C. may be a homopolymer or a copolymer.

The block with a Tg of between 20 and 40° C. may be obtained totally or partly from one or more monomers which are such that the homopolymer prepared from these monomers has a glass transition temperature of between 20 and 40° C.

The block with a Tg of between 20 and 40° C. may be obtained totally or partly from monomers which are such that the corresponding homopolymer has a Tg of greater than or equal to 40° C. and from monomers which are such that the corresponding homopolymer has a Tg of less than or equal to 20° C.

In the case where this block is a homopolymer, it is obtained from monomers (or principal monomers) which are such that the homopolymers prepared from these monomers have glass transition temperatures of between 20 and 40° C. This first block may be a homopolymer composed of a single type of monomer (for which the Tg of the corresponding homopolymer ranges from 20° C. to 40° C.).

The monomers whose homopolymer has a glass transition temperature of between 20 and 40° C. are selected, preferably, from n-butyl methacrylate, cyclodecyl acrylate, neopentyl acrylate and isodecylacrylamide, and mixtures thereof.

In the case where the block with a Tg of between 20 and 40° C. is a copolymer, it is obtained totally or partly from one or more monomers (or principal monomers) the nature and concentration of which are selected such that the Tg of the resulting copolymer is between 20 and 40° C.

Advantageously the block with a Tg of between 20 and 40° C. is a copolymer obtained totally or partly from:
principal monomers whose corresponding homopolymer has a Tg of greater than or equal to 40° C., for example a Tg ranging from 40° C. to 150° C., preferably greater than or equal to 50° C., ranging for example from 50 to 120° C. and better still greater than or equal to 60° C., ranging for example from 60° C. to 120° C., as described above; and/or principal monomers whose corresponding homopolymer has a Tg of less than or equal to 20° C., for example a Tg ranging from −100 to 20° C., preferably less than or equal to 15° C., especially ranging from −80° C. to 15° C. and better still less than or equal to 10° C., for example ranging from −50° C. to 0° C., as described above, the said monomers being selected such that the Tg of the copolymer forming the first block is between 20 and 40° C.

Such principal monomers are selected, for example, from methyl methacrylate, isobornyl acrylate and methacrylate, butyl acrylate and 2-ethylhexyl acrylate, and mixtures thereof.

Preferably the proportion of the second block with a Tg of less than or equal to 20° C. ranges from 10% to 85%, better still from 20% to 70% and even better still from 20% to 50% by weight of the polymer.

Preferably each of the first and second blocks comprises at least one monomer selected from acrylic acid, the esters of acrylic acid, (meth)acrylic acid, the esters of (meth)acrylic acid, and mixtures thereof.

Advantageously each of the first and second blocks is obtained totally from at least one monomer selected from acrylic acid, the esters of acrylic acid, (meth)acrylic acid, the esters of (meth)acrylic acid, and mixtures thereof.

However, each of the blocks may contain in minority proportion at least one constituent monomer of the other block.

Thus the first block may contain at least one constituent monomer of the second block, and vice versa.

Each of the first and/or second blocks may comprise, in addition to the monomers indicated above, one or more other monomers known as additional monomers, which are different from the principal monomers mentioned above.

The nature and amount of this or these additional monomer(s) are selected such that the block in which they are present has the desired glass transition temperature.

This additional monomer is selected, for example, from:
a) hydrophilic monomers such as:
ethylenically unsaturated monomers comprising at least one carboxylic or sulphonic acid function, for instance: acrylic acid, methacrylic acid, crotonic acid, maleic anhydride, itaconic acid, fumaric acid, maleic acid, acrylamidopropanesulphonic acid, vinylbenzoic acid, vinylphosphoric acid, and salts thereof;
ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof;
methacrylates of formula $CH_2=C(CH_3)-COOR_6$ in which $R_6$ represents a linear or branched alkyl group containing from 1 to 4 carbon atoms, such as a methyl, ethyl, propyl or isobutyl group, the said alkyl group being substituted by one or more substituents selected from hydroxyl groups (for instance 2-hydroxypropyl methacrylate and 2-hydroxyethyl methacrylate) and halogen atoms (Cl, Br, I or F), such as trifluoroethyl methacrylate;
methacrylates of formula $CH_2=C(CH_3)-COOR_9$, $R_9$ representing a linear or branched $C_6$ to $C_{12}$ alkyl group in which one or more heteroatoms selected from O, N and S is (are) optionally intercalated, the said alkyl group being substituted by one or more substituents selected from hydroxyl groups and halogen atoms (Cl, Br, I or F);
acrylates of formula $CH_2=CHCOOR_{10}$, $R_{10}$ representing a linear or branched $C_1$ to $C_{12}$ alkyl group substituted by one or more substituents selected from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit from 5 to 30 times, for example methoxy-POE, or $R_{10}$ represents a polyoxyethylenated group comprising from 5 to 30 ethylene oxide units;
b) ethylenically unsaturated monomers comprising one or more silicon atoms, such as methacryloxypropyltrimethoxysilane and methacryloxypropyltris(trimethylsiloxy)silane;
and mixtures thereof.

Additional monomers that are particularly preferred are acrylic acid, methacrylic acid and trifluoroethyl methacrylate, and mixtures thereof.

According to one embodiment, each of the first and second blocks of the block polymer comprises at least one monomer selected from esters of (meth)acrylic acid and optionally at least one additional monomer such as (meth)acrylic acid, and mixtures thereof.

According to another embodiment, each of the first and second blocks of the block polymer is obtained totally from at least one monomer selected from esters of (meth)acrylic acid and optionally at least one additional monomer such as (meth)acrylic acid, and mixtures thereof.

According to one preferred embodiment, the block polymer is a non-silicone polymer, i.e. a polymer free of silicon atoms.

This or these additional monomer(s) generally represent(s) an amount of less than or equal to 30% by weight, for example from 1% to 30% by weight, preferably from 5% to 20% by weight and more preferably from 7% to 15% by weight, relative to the total weight of the first and/or second blocks.

The block polymer may be obtained by free-radical solution polymerization according to the following preparation process:
a portion of the polymerization solvent is introduced into a suitable reactor and heated until the adequate temperature for the polymerization is reached (typically between 60 and 120° C.),
once this temperature is reached, the constituent monomers of the first block are introduced in the presence of a portion of the polymerization initiator,
after a time T corresponding to a maximum degree of conversion of 90%, the constituent monomers of the second block and the rest of the initiator are introduced,
the mixture is left to react for a time T' (ranging from 3 to 6 hours), after which the mixture is cooled to ambient temperature,
the polymer in solution in the polymerization solvent is obtained.

First Embodiment

According to a first embodiment, the block polymer comprises a first block with a Tg of greater than or equal to 40° C., as described above in a), and a second block with a Tg of less than or equal to 20° C., as described above in b).

Preferably the first block with a Tg of greater than or equal to 40° C. is a copolymer obtained from monomers which are such that the homopolymer prepared from these monomers has a glass transition temperature of greater than or equal to 40° C., such as the monomers described above.

Advantageously the second block with a Tg of less than or equal to 20° C. is a homopolymer obtained from monomers which are such that the homopolymer prepared from these monomers has a glass transition temperature of less than or equal to 20° C., such as the monomers described above.

Preferably the proportion of the block with a Tg of greater than or equal to 40° C. ranges from 20% to 90%, better still from 30% to 80% and even better still from 50% to 70% by weight of the polymer.

Preferably the proportion of the block with a Tg of less than or equal to 20° C. ranges from 5% to 75%, preferably from 15% to 50% and better still from 25% to 45% by weight of the polymer.

Thus, according to a first variant, the polymer according to the invention may comprise:
- a first block with a Tg of greater than or equal to 40° C., for example having a Tg ranging from 70 to 110° C., which is a methyl methacrylate/acrylic acid copolymer,
- a second block with a Tg of less than or equal to 20° C., for example ranging from 0 to 20° C., which is a methyl acrylate homopolymer, and
- an intermediate block which is a methyl methacrylate/acrylic acid/methyl acrylate copolymer.

According to a second variant, the polymer according to the invention may comprise:
- a first block with a Tg of greater than or equal to 40° C., for example ranging from 70 to 100° C., which is a methyl methacrylate/acrylic acid/trifluoroethyl methacrylate copolymer,
- a second block with a Tg of less than or equal to 20° C., for example ranging from 0 to 20° C., which is a methyl acrylate homopolymer, and
- an intermediate block which is a methyl methacrylate/acrylic acid/methyl acrylate/trifluoro-ethyl methacrylate random copolymer.

According to a third variant, the polymer according to the invention may comprise:
- a first block with a Tg of greater than or equal to 40° C., for example ranging from 85 to 115° C., which is an isobornyl acrylate/isobutyl methacrylate copolymer,
- a second block with a Tg of less than or equal to 20° C., for example ranging from −85 to −55° C., which is a 2-ethylhexyl acrylate homopolymer, and
- an intermediate block which is an isobornyl acrylate/isobutyl methacrylate/2-ethylhexyl acrylate random copolymer.

According to a fourth variant, the polymer according to the invention may comprise:
- a first block with a Tg of greater than or equal to 40° C., for example ranging from 85 to 115° C., which is an isobornyl acrylate/methyl methacrylate copolymer,
- a second block with a Tg of less than or equal to 20° C., for example ranging from −85 to −55° C., which is a 2-ethylhexyl acrylate homopolymer, and
- an intermediate block which is an isobornyl acrylate/methyl methacrylate/2-ethylhexyl acrylate random copolymer.

According to a fifth variant, the polymer according to the invention may comprise:
- a first block with a Tg of greater than or equal to 40° C., for example ranging from 95 to 125° C., which is an isobornyl acrylate/isobornyl methacrylate copolymer,
- a second block with a Tg of less than or equal to 20° C., for example ranging from −85 to −55° C., which is a 2-ethylhexyl acrylate homopolymer, and
- an intermediate block which is an isobornyl acrylate/isobornyl methacrylate/2-ethylhexyl acrylate random copolymer.

According to a sixth variant, the polymer according to the invention may comprise:
- a first block with a Tg of greater than or equal to 40° C., for example ranging from 85 to 115° C., which is an isobornyl methacrylate/isobutyl methacrylate copolymer,
- a second block with a Tg of less than or equal to 20° C., for example ranging from −35 to −5° C., which is an isobutyl acrylate homopolymer, and
- an intermediate block which is an isobornyl methacrylate/isobutyl methacrylate/isobutyl acrylate random copolymer.

According to a seventh variant, the polymer according to the invention may comprise:
- a first block with a Tg of greater than or equal to 40° C., for example ranging from 95 to 125° C., which is an isobornyl acrylate/isobornyl methacrylate copolymer,
- a second block with a Tg of less than or equal to 20° C., for example ranging from −35 to −5° C., which is an isobutyl acrylate homopolymer, and
- an intermediate block which is an isobornyl acrylate/isobornyl methacrylate/isobutyl acrylate random copolymer.

According to an eighth variant, the polymer according to the invention may comprise:
- a first block with a Tg of greater than or equal to 40° C., for example ranging from 60 to 90° C., which is an isobornyl acrylate/isobutyl methacrylate copolymer,
- a second block with a Tg of less than or equal to 20° C., for example ranging from −35 to −5° C., which is an isobutyl acrylate homopolymer, and
- an intermediate block which is an isobornyl acrylate/isobutyl methacrylate/isobutyl acrylate random copolymer.

The examples which follow illustrate, non-limitatively, polymers corresponding to this first embodiment.

The amounts are expressed in grams.

EXAMPLE 1

Preparation of a poly(methyl methacrylate/acrylic acid/methyl acrylate)polymer 100 g of butyl acetate are introduced into a 1 litre reactor and then the temperature is raised so as to go from ambient temperature (25° C.) to 90° C. over 1 hour.

Subsequently there are added, at 90° C. and over 1 hour, 180 g of methyl methacrylate, 30 g of acrylic acid, 40 g of butyl acetate, 70 g of isopropanol and 1.8 g of 2,5-bis(2-ethylhexanoyl-peroxy)-2,5-dimethylhexane (Trigonox® 141 from Akzo Nobel).

The mixture is held at 90° C. for 1 hour.

Subsequently there are introduced into the above mixture, still at 90° C. and over 1 hour, 90 g of methyl acrylate, 70 g of butyl acetate, 20 g of isopropanol and 1.2 g of 2,5-bis(2-ethylhexanoyl-peroxy)-2,5-dimethylhexane.

The mixture is held at 90° C. for 3 hours, then diluted in 105 g of butyl acetate and 45 g of isopropanol, and then the whole is cooled.

This gives a solution containing 40% polymer active substance in the butyl acetate/isopropanol mixture.

A polymer is obtained which comprises a first, poly(methyl methacrylate/acrylic acid) block with a Tg of 100° C., a second, polymethyl acrylate block with a Tg of 10° C., and an intermediate block which is a methyl methacrylate/acrylic acid/polymethyl acrylate random polymer.

This polymer has a weight-average mass of 52 000 and a number-average mass of 18 000, giving a polydispersity index I of 2.89.

EXAMPLE 2

Preparation of a poly(isobornyl acrylate/isobutyl methacrylate/2-ethylhexyl acrylate)polymer 100 g of isododecane are introduced into a 1 litre reactor and then the temperature is raised so as to go from ambient temperature (25° C.) to 90° C. over 1 hour.

Subsequently there are added, at 90° C. and over 1 hour, 120 g of isobornyl acrylate, 90 g of isobutyl methacrylate, 110 g of isododecane and 1.8 g of 2,5-bis(2-ethylhexanoylperoxy)-2,5-dimethylhexane (Trigonox® 141 from Akzo Nobel).

The mixture is held at 90° C. for 1.5 h.

Subsequently there are introduced into the above mixture, still at 90° C. and over 30 minutes, 90 g of 2-ethylhexyl acrylate, 90 g of isododecane and 1.2 g of 2,5-bis(2-ethylhexanoylperoxy)-2,5-dimethylhexane.

The mixture is held at 90° C. for 3 hours and then the whole is cooled.

This gives a solution containing 50% polymer active substance in isododecane.

A polymer is obtained which comprises a first, poly(isobornyl acrylate/isobutyl methacrylate) block with a Tg of 80° C., a second, poly-2-ethylhexyl acrylate block with a Tg of −70° C., and an intermediate block which is an isobornyl acrylate/isobutyl methacrylate/2-ethylhexyl acrylate random polymer.

This polymer has a weight-average mass of 77 000 and a number-average mass of 19 000, giving a polydispersity index I of 4.05.

EXAMPLE 3

Preparation of a poly(isobornyl acrylate/methyl methacrylate/2-ethylhexyl acrylate) polymer 100 g of isododecane are introduced into a 1 litre reactor and then the temperature is raised so as to go from ambient temperature (25° C.) to 90° C. over 1 hour.

Subsequently there are added, at 90° C. and over 1 hour, 150 g of isobornyl acrylate, 60 g of methyl methacrylate, 110 g of isododecane and 1.8 g of 2,5-bis(2-ethylhexanoylperoxy)-2,5-dimethylhexane (Trigonox® 141 from Akzo Nobel).

The mixture is held at 90° C. for 1.5 h.

Subsequently there are introduced into the above mixture, still at 90° C. and over 30 minutes, 90 g of 2-ethylhexyl acrylate, 90 g of isododecane and 1.2 g of 2,5-bis(2-ethylhexanoylperoxy)-2,5-dimethylhexane.

The mixture is held at 90° C. for 3 hours and then the whole is cooled.

This gives a solution containing 50% polymer active substance in isododecane.

A polymer is obtained which comprises a first, poly(isobornyl acrylate/methyl methacrylate) block with a Tg of 100° C., a second, poly-2-ethylhexyl acrylate block with a Tg of −70° C., and an intermediate block which is an isobornyl acrylate/methyl methacrylate/2-ethylhexyl acrylate random polymer.

This polymer has a weight-average mass of 76 500 and a number-average mass of 22 000, giving a polydispersity index I of 3.48.

EXAMPLE 4

Preparation of a poly(isobornyl acrylate/isobornyl methacrylate/2-ethylhexyl acrylate)polymer 100 g of isododecane are introduced into a 1 litre reactor and then the temperature is raised so as to go from ambient temperature (25° C.) to 90° C. over 1 hour.

Subsequently there are added, at 90° C. and over 1 hour, 105 g of isobornyl acrylate, 105 g of isobornyl methacrylate, 110 g of isododecane and 1.8 g of 2,5-bis(2-ethylhexanoylperoxy)-2,5-dimethylhexane (Trigonox® 141 from Akzo Nobel).

The mixture is held at 90° C. for 1.5 h.

Subsequently there are introduced into the above mixture, still at 90° C. and over 30 minutes, 90 g of 2-ethylhexyl acrylate, 90 g of isododecane and 1.2 g of 2,5-bis(2-ethylhexanoylperoxy)-2,5-dimethylhexane.

The mixture is held at 90° C. for 3 hours and then the whole is cooled.

This gives a solution containing 50% polymer active substance in isododecane.

A polymer is obtained which comprises a first, poly(isobornyl acrylate/isobornyl methacrylate) block or sequence with a Tg of 110° C., a second, poly-2-ethylhexyl acrylate block with a Tg of −70° C., and an intermediate block which is an isobornyl acrylate/isobornyl methacrylate/2-ethylhexyl acrylate random polymer.

This polymer has a weight-average mass of 103 900 and a number-average mass of 21 300, giving a polydispersity index I of 4.89.

Second Embodiment

According to a second embodiment, the block polymer comprises a first block with a glass transition temperature (Tg) of between 20 and 40° C., in accordance with the blocks described in c), and a second block with a glass transition temperature of less than or equal to 20° C., as described above in b), or a glass transition temperature of greater than or equal to 40° C., as described in a) above.

Preferably the proportion of the first block with a Tg of between 20 and 40° C. ranges from 10% to 85%, better still from 30% to 80% and even better still from 50% to 70% by weight of the polymer.

When the second block is a block with a Tg of greater than or equal to 40° C., it is preferably present in a proportion ranging from 10% to 85% by weight, better still from 20% to 70% and even better still from 30% to 70% by weight of the polymer.

When the second block is a block with a Tg of less than or equal to 20° C., it is preferably present in a proportion ranging from 10% to 85% by weight, better still from 20% to 70% and even better still from 20% to 50% by weight of the polymer.

Preferably the first block with a Tg of between 20 and 40° C. is a copolymer obtained from monomers which are such that the corresponding homopolymer has a Tg of greater than or equal to 40° C., and from monomers which are such that the corresponding homopolymer has a Tg of less than or equal to 20° C.

Advantageously the second block with a Tg of less than or equal to 20° C. or with a Tg of greater than or equal to 40° C. is a homopolymer.

Thus, according to a first variant of this second embodiment, the block polymer may comprise:

a first block with a Tg of between 20 and 40° C., for example with a Tg of 25 to 39° C., which is a copolymer comprising at least one methyl acrylate monomer, at least one methyl methacrylate monomer and at least one acrylic acid monomer, a second block with a Tg of greater than or equal to 40° C., for example ranging from 85 to 125° C., which is a homopolymer composed of methyl methacrylate monomers, and an intermediate block comprising at least one methyl acrylate or methyl methacrylate monomer, and an intermediate block comprising methyl methacrylate, at least one acrylic acid monomer and at least one methyl acrylate monomer.

According to a second variant of this second embodiment, the block polymer may comprise:

a first block with a Tg of between 20 and 40° C., for example with a Tg of 21 to 39° C., which is a copolymer comprising isobornyl acrylate/isobutyl methacrylate/2-ethylhexyl acrylate, a second block with a Tg of less than or equal to 20° C., for example ranging from −65 to −35° C., which is a methyl methacrylate homopolymer, and an intermediate block which is an isobornyl acrylate/isobutyl methacrylate/2-ethylhexyl acrylate random copolymer.

According to a third variant of this second embodiment, the block polymer may comprise:

a first block with a Tg of between 20 and 40° C., for example with a Tg of from 21 to 39° C., which is an isobornyl acrylate/methyl acrylate/acrylic acid copolymer, a second block with a Tg of greater than or equal to 40° C., for example ranging from 85 to 115° C., which is an isobornyl acrylate homopolymer, and an intermediate block which is an isobornyl acrylate/methyl acrylate/acrylic acid random copolymer.

By way of illustration, but without limitation, the polymers corresponding to this second embodiment may be realised as follows.

EXAMPLE 5

Preparation of a poly(methyl methacrylate/methyl acrylate/acrylic acid)polymer 100 g of butyl acetate are introduced into a 1 litre reactor and then the temperature is raised so as to go from ambient temperature (25° C.) to 90° C. over 1 hour.

Subsequently there are added, at 90° C. and over 1 hour, 50.4 g of methyl methacrylate, 21 g of acrylic acid, 138.6 g of methyl acrylate, 40 g of butyl acetate, 70 g of isopropanol and 1.8 g of 2,5-bis(2-ethylhexanoylperoxy)-2,5-dimethylhexane (Trigonox® 141 from Akzo Nobel).

The mixture is held at 90° C. for 1 hour.

Subsequently there are introduced into the above mixture, still at 90° C. and over 1 hour, 90 g of methyl methacrylate, 70 g of butyl acetate, 20 g of isopropanol and 1.2 g of 2,5-bis(2-ethylhexanoyl-peroxy)-2,5-dimethylhexane.

The mixture is held at 90° C. for 3 hours and then diluted with 105 g of butyl acetate and 45 g of isopropanol, and the whole is then cooled.

This gives a solution containing 40% polymer active substance in the butyl acetate/isopropanol mixture.

The polymer obtained comprises a first poly(methyl acrylate/methyl methacrylate/acrylic acid) block having a Tg of 35° C., a second poly(methyl methacrylate) block having a Tg of 100° C. and an intermediate block which is a methyl methacrylate/acrylic acid/polymethyl acrylate random polymer.

EXAMPLE 6

Preparation of a poly(isobornyl acrylate/isobutyl methacrylate/2-ethylhexyl acrylate)polymer 100 g of isododecane are introduced into a 1 litre reactor and then the temperature is raised so as to go from ambient temperature (25° C.) to 90° C. over 1 hour.

Subsequently there are added, at 90° C. and over 1 hour, 54 g of isobornyl acrylate, 75.6 g of isobutyl methacrylate, 50.4 g of 2-ethylhexyl acrylate, 110 g of isododecane and 1.8 g of 2,5-bis(2-ethylhexanoylperoxy)-2,5-dimethylhexane (Trigonox® 141 from Akzo Nobel).

The mixture is held at 90° C. for 1.5 h.

Subsequently there are introduced into the above mixture, still at 90° C. and over 1 hour, 120 g of 2-ethylhexyl acrylate, 90 g of isododecane and 1.2 g of 2,5-bis(2-ethylhexanoylperoxy)-2,5-dimethylhexane.

The mixture is held at 90° C. for 3 hours and then diluted and the whole is then cooled.

This gives a solution containing 50% of polymer active substance in isododecane.

A polymer is obtained which comprises a first poly (isobornyl acrylate/isobutyl methacrylate/2-ethyl-hexyl acrylate) block having a Tg of 25° C., a second poly-2-ethylhexyl acrylate block having a Tg of −50° C. and an intermediate block which is an isobornyl acrylate/isobutyl methacrylate/2-ethylhexyl acrylate random polymer.

The composition according to the invention contains preferably from 0.1% to 60% by weight of active substance (or solids) of the polymer, preferably from 0.5% to 50% by weight and more preferably from 1% to 40% by weight.

Gelling Agent

The composition of the invention also comprises at least one agent for gelling the organic liquid medium of the composition. The gelling agent may increase the viscosity of the organic liquid medium and may lead to a solid or flowable composition when introduced into the said organic liquid medium.

The gelling agent may be selected from gelling agents in polymeric form and gelling agents in mineral form.

In one embodiment the gelling agent is not soluble in an aqueous phase or in water.

The gelling agent according to the present invention is selected preferably from the group consisting of agents which gel via chemical crosslinking and agents which gel via physical crosslinking.

Gelling Agents which Gel Via Chemical Crosslinking

According to one embodiment, preference is given to crosslinked elastomeric polyorganosiloxanes of three-dimensional structure, such as MQ silicone resins, polyalkylsesquioxanes, especially polymethyl-sesquioxanes, and resins crosslinked via hydro-silylation. These silicone resins may carry hydrophilic groups, such as polyoxyethylene or copoly (oxyethylene/oxypropylene).

As polyorganosiloxanes which can be used in the invention, mention may be made of the crosslinked elastomeric polyorganosiloxanes described in application EP-A-0 295 886, the disclosure of which is incorporated in this text by reference. According to that application they are obtained by addition reaction and crosslinking, in the presence of a platinum-type catalyst, of at least:

(a) a polyorganosiloxane having at least two $C_2$ to $C_6$ lower alkenyl groups per molecule; and
(b) a polyorganosiloxane having at least two hydrogen atoms bonded to a silicon atom per molecule. It is also possible to use the polyorganosiloxanes described in U.S. Pat. No. 5,266,321, the disclosure of which is incorporated in this text by reference. According to that patent they are selected in particular from:
i) polyorganosiloxanes comprising $R_2SiO$ and $RSiO_{1.5}$ units and optionally $R_3SiO_{0.5}$ and/or $SiO_2$ units, in which the radicals $R_1$, independently of one another, are selected from a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1/1 to 30/1;
ii) polyorganosiloxanes which are insoluble and swellable in silicone oil, obtained by addition of a polyorganohydrosiloxane (1) and a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic. Optionally these polyorganosiloxanes can comprise from 1 to 40 oxyalkylene groups, such as oxypropylene and/or oxyethylene groups.

As examples of polyorganosiloxanes which can be used according to the invention, mention may be made of those sold or made under the names KSG6 from Shin-Etsu, Trefil E-505C or Trefil E-506C from Dow Corning, Gransil from Grant Industries (SR-CYC, SR DMF10, SR-DC556) or those sold in the form of preconstituted gels (KSG15, KSG17, KSG16, KSG18 and KSG21 from Shin-Etsu, Gransil SR 5CYC gel, Gransil SR DMF 10 gel, Gransil SR DC556 gel, SF 1204 and JK 113 from General Electric. A mixture of these commercial products may also be used.

Gelling Agents which Gel Via Physical Crosslinking

Gelling agents which gel via physical crosslinking, particularly by molecular agitation, hydrogen interactions or dipolar interactions, and also fat-soluble polymers having liquid crystal groups, are preferred.

Gelling agents which gel via molecular agitation are polymers having high molecular weights, preferably greater than 500 000, such as silicone gums.

The silicone gum may correspond to the formula:

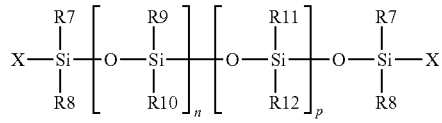

in which:
$R_7$, $R_8$, $R_{11}$ and $R_{12}$ are identical or different and each is selected from alkyl radicals containing from 1 to 6 carbon atoms,
$R_9$ and $R_{10}$ are identical or different and each is selected from alkyl radicals containing from 1 to 6 carbon atoms and aryl radicals,
X is selected from alkyl radicals containing from 1 to 6 carbon atoms, a hydroxyl radical and a vinyl radical, n and p are selected so as to give the silicone gum a viscosity of greater than 100 000 mPa·s, such as greater than 500 000 mPa·s.
In general, n and p can each take values ranging from 0 to 5000, such as from 0 to 3000.

Among the silicone gums which can be used as a gelling agent according to the invention, mention may be made of those for which:
the substituents $R_7$ to $R_{12}$ and X represent a methyl group, p=0 and n=2700, such as the product sold or made under the name SE30 by the company General Electric,
the substituents $R_7$ to $R_{12}$ and X represent a methyl group, p=0 and n=2300, such as the product sold or made under the name AK 500 000 by the company Wacker,
the substituents $R_7$ to $R_{12}$ represent a methyl group, the substituent X represents a hydroxyl group, p=0 and n=2700, in the form of a 13% solution in cyclopentasiloxane, such as the product sold or made under the name Q2-1401 by the company Dow Corning,
the substituents $R_7$ to $R_{12}$ represent a methyl group, the substituent X represents a hydroxyl group, p=0 and n=2700, in the form of 13% solution in polydimethylsiloxane, such as the product sold or made under the name Q2-1403 by the company Dow Corning, and
the substituents $R_7$, $R_8$, $R_{11}$, $R_{12}$ and X represent a methyl group and the substituents $R_9$ and $R_{10}$ represent an aryl group, such that the molecular weight of the gum is approximately 600 000, for example the product sold or made under the name 761 by the company Rhône-Poulenc (Rhodia Chimie).

Gelling agents which gel the organic liquid medium via hydrogen interactions are selected preferably from the group consisting of:
aminosilicone polymers having triazinyl groups or pyrimidinyl groups bonded to amino groups of aminosilicones, as described in patent application EP 0 751 170, the disclosure of which is incorporated in this text by reference,
non-silicone polyamides whose ends carry ester or triamide functions, such as the compounds described in patents and patent applications U.S. Pat. Nos. 5,783, 657, 6,268,466, WO 01/95871, WO 00/40216, U.S. Pat. No. 2002/0035237 and EP 1 068 856, the disclosure of which is incorporated in this text by reference,
polyurethanes, such as the compounds described in patent applications DE 100 22 247 and FR 2 814 365, the disclosure of which is incorporated in this text by reference, and
vinyl and/or (meth)acrylic polymers carrying side groups which are able to give rise to mutual hydrogen interactions, such as the compounds described in patent application WO 93/01797, the disclosure of which is incorporated in this text by reference.

Gelling agents may also be selected from the group consisting of:
copolymers such as polystyrene-silicone or polyethylene-silicone, described in patents U.S. Pat. Nos. 6,225,390, 6,160,054, 6,174,968 and 6,225,390, the disclosures of which are incorporated in this text by reference,
copolymers comprising a silicone block and another block or graft which is polyvinylic or poly(meth)acrylic, such as those described in patents U.S. Pat. Nos. 5,468,477 and 5,725,882, the disclosures of which are incorporated in this text by reference,
polymers or copolymers resulting from the polymerization or copolymerization of an ethylenic monomer containing one or more ethylenic, preferably conjugated, bonds (or dienes),
polymers or copolymers resulting from the polymerization or copolymerization of an ethylenic monomer; in particular it is possible to use vinyl, acrylic or methacrylic copolymers. The ethylenic gelling agent may comprise, for example, a styrene (S) block and an alkylstyrene (AS) block, and a block selected from ethylene/butylene (EB), ethylene/propylene (EP), butadiene (B), isoprene (I), acrylate (A) and methacrylate (MA) blocks or a combination of these blocks.

In one embodiment a copolymer comprising at least one styrene block is used as gelling agent. A triblock copolymer, and in particular those of the polystyrene/polyisoprene or polystyrene/polybutadiene type, such as those sold or made under the name "Luvitol HSB" by BASF and those of the polystyrene/copoly(ethylene-propylene) type or, alternatively, those of the polystyrene/copoly(ethylene/butylene) type, such as those sold or made under the brand name "Kraton" by Shell Chemical Co. or Gelled Permethyl 99A by Penreco, may be used. Styrene-methacrylate copolymers may also be used.

As an ethylenic gelling agent which can be used in the composition of the invention, mention may be made, for example, of Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58, Gelled Permethyl 99A-753-59, Versagel 5970 and Versagel 5960 from Penreco, and OS 129880, OS 129881 and OS 84383 from Lubrizol (styrene-methacrylate copolymer).

Diblocks or triblocks such as polystyrene-copoly(ethylene/propylene) or polystyrene-copoly(ethylene/butylene), such as those described in patent applications WO 98/38981 and US 2002/0055562 are also included in the present invention.

Gelling agents which gel via dipolar interactions are selected preferably from the compounds described in documents WO 01/30886 and U.S. Pat. No. 6,228,967, the disclosures of which are incorporated in this text by reference. The ionized groups in the said compounds, for example the zwitterionic groups, create the said dipolar interactions.

Gelling agents such as the fat-soluble polymers having liquid crystal groups are also preferred according to the present invention, particularly fat-soluble polymers whose skeleton is of silicone, vinyl and/or (meth)acrylic type, and which possess liquid crystal side groups, especially the compounds described in patent application FR 2 816 503, the disclosure of which is incorporated in this text by reference.

In another embodiment the gelling agent may be in mineral form.

The gelling agent may be a modified clay. As modified clays which can be used, mention may be made of hectorites modified with an ammonium chloride of a $C_{10}$ to $C_{22}$ fatty acid, such as a hectorite modified with distearyldimethylammonium chloride, also known as bentonite of quaternium-18, such as the products sold or made under the names Bentone 34 by the company Rheox, Claytone XL, Claytone 34 and Claytone 40 sold or made by the company Southern Clay, modified clays known under the name quaternium-18 bentonites and benzalkonium bentonites and sold or made under the names Claytone HT, Claytone GR and Claytone PS by the company Southern Clay, clays modified with stearyldi-methylbenzoylammonium chloride, known as stearalkonium bentonites, such as the products sold or made under the names Claytone APA and Claytone AF by the company Southern Clay, and Baragel 24, sold or made by the company Rheox.

As other mineral gelling agents which can be used in the invention, mention may be made of silica, such as fumed silica. The fumed silica may have a particle size which may be nanometric or micrometric, for example ranging from approximately 5 nm to 200 nm.

Fumed silicas may be obtained by high-temperature hydrolysis of a volatile silicon compound in an oxyhydrogen flame, producing a finely divided silica. This process allows hydrophilic silicas to be obtained which possess a large number of silanol groups on their surface. The silanol groups may be replaced, for example, by hydrophobic groups: this then gives a hydrophobic silica. The hydrophobic groups may be:

trimethylsiloxyl groups, which are obtained in particular by treating fumed silica in the presence of hexamethyldisilazane. The silicas thus treated are known as "silica silylate" according to the CTFA (6th edition, 1995). They are sold or made, for example, under the references "Aerosil R812®" by the company Degussa, and "CAB-O-SIL TS-530®" by the company Cabot;

dimethylsilyloxyl or polydimethylsiloxane groups, which are obtained in particular by treating fumed silica in the presence of polydimethyldisiloxane or dimethyldichlorosilane. The silicas thus treated are known as "silica dimethylsilylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot;

groups derived from the reaction of fumed silica with silane alkylates or siloxanes. These treated silicas are, for example, the products sold or made under the reference "Aerosil R805®" by the company Degussa.

According to the invention a hydrophobic silica, such as a fumed silica, may be used as gelling agent.

The gelling agent may be used, for example, in concentrations ranging from 0.05% to 35% of the total weight of the composition, for example from 0.5% to 20% or from 1% to 10%.

The composition according to the invention may comprise a hydrophilic medium comprising water or a mixture of water and hydrophilic organic solvent(s) such as alcohols and especially linear or branched lower monoalcohols having from 2 to 5 carbon atoms such as ethanol, isopropanol or n-propanol, and polyols such as glycerol, diglycerol, propylene glycol, sorbitol, pentylene glycol, and polyethylene glycols, or else $C_2$ ethers and $C_2$-$C_4$ aldehydes which are hydrophilic.

The water or the mixture of water and hydrophilic organic solvents may be present in the composition according to the invention in an amount ranging from 0.1% to 99% by weight, relative to the total weight of the composition, and preferably from 10% to 80% by weight.

The composition according to the invention comprises an organic liquid medium which is cosmetically acceptable (acceptable tolerance, toxicology and feel).

According to one particularly preferred embodiment the organic liquid medium of the composition comprises at least one organic solvent, which is the, or one of the, polymerization solvent(s) of the block polymer as described above. Advantageously the said organic solvent is the majority liquid by weight in the organic liquid medium of the cosmetic composition.

According to one embodiment, the organic liquid medium comprises fatty substances which are liquid at ambient temperature (25° C. in general). These liquid fatty substances may be animal, vegetable, mineral or synthetic in origin.

As fatty substances which are liquid at ambient temperature, often called oils, which can be used in the invention mention may be made of: hydrocarbon oils of animal origin, such as perhydrosqualene; vegetable hydrocarbon oils, such as liquid triglycerides of fatty acids of 4 to 10 carbon atoms, such as heptanoic or octanoic acid triglycerides, or else sunflower oil, corn oil, soya oil, grape seed oil, sesame oil, apricot oil, macadamia oil, castor oil, avocado oil, caprylic/capric acid triglycerides, jojoba oil, karite butter; linear or branched hydrocarbons, of mineral or synthetic origin, such as liquid paraffins and derivatives thereof, Vaseline, polydecenes, hydrogenated polyisobutene such as parleam; the synthetic esters and ethers particularly of fatty acids, such as, for example, purcellin oil, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, and heptanoates, octanoates and decanoates of fatty alcohols; polyol esters such as propylene glycol dioctanoate, neopentyl glycol diheptanoate and diethylene glycol diisononanoate; and pentaerythritol esters; fatty alcohols having 12 to 26 carbon atoms, such as octyldodecanol, 2-butyloctanol, 2-hexyldecanol, 2-undecylpentadecanol, and oleyl alcohol; partially hydrocarbon-based and/or silicone-based fluoro oils; silicone oils, such as volatile or non-volatile polydimethylsiloxanes (PDMS) that are linear or cyclic, such as cyclomethicones, dimethicones, optionally including a phenyl group, such as phenyl trimethicones, phenyltrimethylsiloxydiphenylsiloxanes, diphenylmethyldimethyltrisiloxanes, diphenyldimethicones, phenyldimethicones and polymethylphenylsiloxanes; and mixtures thereof.

These oils may be present in an amount ranging from 0.01% to 90%, and better still from 0.1% to 85% by weight, relative to the total weight of the composition.

The organic liquid medium of the composition according to the invention may also comprise one or more organic solvents which are cosmetically acceptable (acceptable tolerance, toxicology and feel).

These solvents may be generally present in an amount ranging from 0.1% to 90%, more preferably from 10% to 90% by weight, relative to the total weight of the composition, and better still from 30% to 90%.

As solvents which can be used in the composition of the invention mention may be made, besides the aforementioned hydrophilic organic solvents, of ketones which are liquid at ambient temperature, such as methyl ethyl ketone, methyl isobutyl ketone, diisobutyl ketone, isophorone, cyclohexanone and acetone; propylene glycol ethers which are liquid at ambient temperature, such as propylene glycol monomethyl ether, propylene glycol monomethyl ether acetate, and dipropylene glycol mono-n-butyl ether; short-chain esters (having 3 to 8 carbon atoms in total), such as ethyl acetate, methyl acetate, propyl acetate, n-butyl acetate and isopentyl acetate; ethers which are liquid at ambient temperature, such as diethyl ether, dimethyl ether or dichlorodiethyl ether; alkanes which are liquid at ambient temperature, such as decane, heptane, dodecane, isododecane and cyclohexane; aromatic cyclic compounds which are liquid at ambient temperature, such as toluene and xylene; and aldehydes which are liquid at ambient temperature, such as benzaldehyde and acetaldehyde, and mixtures thereof.

Besides the block polymer described above, the composition may comprise an additional polymer such as a film-forming polymer. According to the present invention a "film-forming polymer" is a polymer capable of forming, by itself or in the presence of an auxiliary film-forming agent, a continuous and adherent film on a support, particularly on keratin materials.

Among the film-forming polymers which can be used in the composition of the present invention, mention may be made of synthetic polymers, of free-radical type or polycondensate type, and of polymers of natural origin, and mixtures thereof. As film-forming polymer, mention may be made in particular of acrylic polymers, polyurethanes, polyesters, polyamides, polyureas and cellulosic polymers such as nitrocellulose.

The polymer may be combined with one or more auxiliary film-forming agents. A film-forming agent of this kind may be selected from all of the compounds known to the person skilled in the art as being capable of fulfilling the desired function, and in particular may be selected from plasticizers and coalescers.

The composition according to the invention may include at least one wax. By wax in the sense of the present invention is meant a lipophilic compound which is solid at ambient temperature (25° C.), exhibits a reversible solid/liquid state change and has a melting point greater than or equal to 30° C. and possibly up to 120° C.

The melting point of the wax can be measured by means of a differential scanning calorimeter (DSC), an example being the calorimeter sold under the name DSC 30 by the company Mettler.

The waxes may be hydrocarbon waxes, fluoro waxes and/or silicone waxes and may be vegetable, mineral, animal and/or synthetic in origin. In particular the waxes have a melting point of more than 25° C. and better still more than 45° C.

As wax which can be used in the composition of the invention mention may be made of beeswax, carnauba wax or candelilla wax, paraffin, microcrystalline waxes, ceresin or ozokerite; synthetic waxes such as polyethylene waxes or Fischer-Tropsch waxes, and silicone waxes such as the alkyl- or alkoxydimethicones having 16 to 45 carbon atoms.

The nature and amount of the solid fatty substances are a function of the desired mechanical properties and textures. By way of indication the composition may contain from 0% to 50% by weight of waxes, relative to the total weight of the composition, and better still from 1% to 30% by weight.

The composition according to the invention may further comprise one or more colorants selected from water-soluble dyes and pulverulent colorants such as pigments, nacres and flakes, which are well known to the person skilled in the art. The colorants may be present in the composition in an amount ranging from 0.01% to 50% by weight, relative to the weight of the composition, preferably from 0.01% to 30% by weight.

By pigments are meant particles of any form, white or coloured, organic or inorganic, which are insoluble in the physiological medium and are intended for colouring the composition.

By nacres are meant iridescent particles of any form that are produced in particular by certain molluscs in their shell, or else are synthesized.

The pigments may be white or coloured, organic and/or inorganic. Among inorganic pigments mention may be made of titanium dioxide, optionally in surface-treated form, zirconium oxide or cerium oxide, and also zinc oxide, iron oxides (black, yellow or red) or chromium oxide, manganese violet, ultramarine blue, chromium hydrate and ferric blue, and metal powders such as aluminium powder and copper powder.

Among organic pigments mention may be made of carbon black, D & C pigments, and the cochineal carmine-based lakes of barium, strontium, calcium and aluminium.

Mention may also be made of effect pigments, such as particles comprising an organic or inorganic, natural or synthetic substrate, for example glass, acrylic resins, polyester, polyurethane, polyethylene terephthalate, ceramics or aluminas, the said substrate being uncovered or covered with metallic substances such as aluminium, gold, silver, platinum, copper or bronze, or with metal oxides such as titanium dioxide, iron oxide or chromium oxide, and mixtures thereof.

The nacreous pigments may be selected from white nacreous pigments such as titanium-covered mica, or bismuth oxychloride, coloured nacreous pigments such as titanium mica covered with iron oxides, titanium mica covered with, in particular, ferric blue or chromium oxide, titanium mica covered with an organic pigment of the aforementioned type, and also nacreous pigments based on bismuth oxychloride. It is also possible to use interference pigments, especially those which are liquid-crystal pigments or multi-layer pigments.

The water-soluble dyes are, for example, beetroot juice and methylene blue.

The composition according to the invention may further comprise one or more fillers, particularly in an amount ranging from 0.01% to 50% by weight, relative to the total weight of the composition, preferably ranging from 0.01% to 30% by weight. By fillers are meant particles of any form, colourless or white, mineral or synthetic, which are insoluble in the medium of the composition irrespective of the temperature at which the composition is manufactured. These fillers serve in particular to modify the rheology or texture of the composition.

The fillers may be organic or inorganic and may be in any form, platelet-shaped, spherical or oblong, irrespective of the crystallographic form (for example leaf, cubic, hexagonal, orthorhombic, etc.). Mention may be made of talc, mica, silica, kaolin, polyamide (Nylon®) powders (Orgasol® from Atochem), poly-β-alanine and polyethylene, the powders of polymers of tetrafluoroethylene (Teflon®), lauroyl-lysine, starch, boron nitride, hollow polymeric microspheres such as those of polyvinylidene chloride/acrylonitrile, for instance Expancel® (Nobel Industrie), acrylic acid copolymers (Polytrap® from the company Dow Corning) and silicone resin microbeads (Tospearls® from Toshiba, for example), elastomeric polyorganosiloxane particles, precipitated calcium carbonate, magnesium carbonate and magnesium hydrocarbonate, hydroxyapatite, hollow silica microspheres (Silica Beads® from Maprecos), ceramic or glass microcapsules, metal soaps derived from organic carboxylic acids having 8 to 22 carbon atoms, preferably 12 to 18 carbon atoms, for example zinc stearate, magnesium stearate or lithium stearate, zinc laurate and magnesium myristate.

The composition according to the invention may be in the form in particular of a stick, suspension, dispersion, solution, gel, emulsion, especially oil-in-water (O/W) or water-in-oil (W/O), or multiple (O/W/O or polyol/O/W or W/O/W), emulsion, or in the form of a cream, paste or mousse, or a vesicle dispersion, particularly of ionic or nonionic lipids, or a two-phase or multi-phase lotion, a spray, powder or paste, especially a flexible paste (in particular a paste having a dynamic viscosity at 25° C. of the order of 0.1 to 40 Pa·s at a shear rate of 200 s$^{-1}$, after 10 minutes of measurement in cone/plate geometry). The composition may be anhydrous: for example, it may be an anhydrous paste.

The person skilled in the art will be able to select the appropriate type of formulation, and the method of preparing it, on the basis of his or her general knowledge, taking into account, on the one hand, the nature of the constituents used, and especially their solubility in the vehicle, and, on the other hand, the application envisaged for the composition.

The composition according to the invention may be a makeup composition such as products for the complexion (foundations), rouges, eyeshadows, lipsticks, concealers, blushers, mascaras, eyeliners, eyebrow makeup products, lip pencils, eye pencils, nail products, such as nail varnishes, body makeup products or hair makeup products (hair lacquer or mascara).

The composition according to the invention may also be a facial or bodily skincare product, in particular a sun product or skin colouring product (such as a self-tanning product).

The present invention likewise provides a cosmetic kit comprising:
a container delimiting at least one compartment, the said container being closed by a closing element; and
a composition as described above disposed inside the said compartment.

The container may be in any appropriate form. It may in particular be in the form of a bottle, tube, jar, case, box, sachet or carton.

The closing element may be in the form of a removable stopper, a lid, a cap, a tear-off strip or a capsule, particularly of the type comprising a body attached to the container and a cover cap articulated on the body. It may also be in the form of an element for selectively closing the container, particularly a pump, valve or valve flap.

The container may be combined with an applicator, particularly in the form of a brush comprising an arrangement of bristles held by a twisted wire. A twisted brush of this kind is described in particular in patent U.S. Pat. No. 4,887,622. It may also be in the form of a comb comprising a plurality of application elements, obtained in particular from moulding. Combs of this kind are described, for example, in patent FR 2 796 529. The applicator may be in the form of a fine brush, as described, for example, in patent FR 2 722 380. The applicator may be in the form of a block of foam or elastomer, a felt or a spatula. The applicator may be free (tuft or sponge) or of one piece with a rod carried by the closing element, as described, for example, in patent U.S. Pat. No. 5,492,426. The applicator may be of one piece with the container, as described, for example, by patent FR 2 761 959.

The product may be accommodated directly in the container, or indirectly. By way of example, the product may be arranged on an impregnated support, particularly in the form of a wipe or pad, and arranged (in unitary or plural form) in a box or in a sachet. A support of this kind, incorporating the product, is described for example in patent application WO 01/03538.

The closing element may be coupled to the container by screwing. Alternatively the coupling between the closing element and the container is performed other than by screwing, in particular via a bayonet mechanism, by snap-fastening, gripping, welding, adhesive bonding, or by magnetic attraction. By "snap-fastening" is meant, in particular, any system involving the traversal of a bead or cord of material by elastic deformation of a portion, particularly of the closing element, followed by return to the elastically unstressed position of the said portion after the traversal of the bead or cord.

The container may be at least partly made of thermoplastic material. Examples that may be mentioned of thermoplastic materials include polypropylene and polyethylene.

Alternatively the container is made of a non-thermoplastic material, particularly of glass or of metal (or alloy).

The container may be one with rigid walls or may have deformable walls, particularly in the form of a tube or tubular bottle.

The container may include means intended for distributing, or facilitating the distribution of, the composition. By way of example, the container may have walls which are deformable so as to allow the composition to exit in response to a positive pressure inside the container, this positive pressure being brought about by elastic (or non-elastic) squeezing of the container's walls. Alternatively, and particularly when the product is in the form of a stick, the product may be driven by a piston mechanism. Still in the case of a stick, particularly a makeup product stick (lipstick, foundation, etc.), the container may include a mechanism, especially a rack mechanism, or one with a threaded rod, or with a helical groove, which is capable of displacing a stick in the direction of the said opening. A mechanism of this kind is described for example in patent FR 2 806 273 or in patent FR 2 775 566. A mechanism of this kind for a liquid product is described in patent FR 2 727 609.

The container may be composed of a carton with a base delimiting at least one housing accommodating the composition, and a lid, particularly a lid articulated on the base, which is capable of covering the said base, at least in part. A carton of this kind is described for example in patent application WO 03/018423 or in patent FR 2 791 042.

The container may be equipped with a drainer arranged in the region of the opening of the container. A drainer of this kind allows the applicator to be wiped and optionally allows the rod, which may be of one piece with it, to be wiped. A drainer of this kind is described for example in patent FR 2 792 618.

The composition may be at the atmospheric pressure inside the container (at ambient temperature) or may be in pressurized form, particularly by means of a propellent gas (aerosol). In the latter case the container is equipped with a valve (of the type used for aerosols).

The content of the patents or patent applications cited above is incorporated by reference into the present application.

The examples which follow illustrate, without limitation, the compositions according to the invention.

EXAMPLE 7

Liquid Lipstick

| INGREDIENTS | % BY MASS |
| --- | --- |
| Polymer from Example 4 | 50.0 |
| Silica (Aerosil R 972 ®, Degussa) | 5.0 |
| Isododecane gelled with an ethylene/propylene/styrene copolymer and a butylene/ethylene/styrene copolymer (Versagel ® MD 970, Penreco) | 7.0 |
| Hydrogenated polyisobutene | 2.1 |
| Octyldodecanol | 0.9 |
| Phenyltrimethicone (DC 556, 20 cSt, Dow Corning) | 2.1 |
| Isododecane | 28.3 |
| Vinylpyrrolidone/1-eicosene copolymer (Antaron V-220 ®, ISP) | 1.2 |
| Pigments | 3.0 |
| Perfume | qs |

The formula exhibits a much greater viscosity than the reference without gelling agent. It can also be applied without difficulty using a foam applicator, and leads to a homogeneous deposit.

EXAMPLE 8

Sun Composition

| Ingredients | (% by weight) |
| --- | --- |
| Glycerol | 6 |
| Propylene glycol | 6 |
| Acrylates/$C_{10}$-$C_{30}$ alkyl acrylate copolymer PEMULEN TR-2 (Noveon) | 0.3 |
| Ammonium polyacryloyldimethyltaurate polymer (HOSTACERIN AMPS - Clariant) | 0.3 |
| Cyclohexasiloxane (DOW CORNING 246 FLUID - Dow Corning) | 6 |
| Xanthan gum RHODICARE XC (Rhodia) | 0.1 |
| Terephthalylidene dicamphor sulphonic acid (MEXORYL SX - Chimex) | 1.5 |
| Triethanolamine | qs |
| Octocrylene (UVINUL N539 - BASF) | 10 |
| Butylmethoxydibenzoylmethane (Parsol 1789 - Roche Vitamines) | 2.5 |
| Drometrizole trisiloxane (MEXORYL XL - Chimex) | 1.5 |
| $C_{12}$-$C_{15}$ alkyl benzoate (FINSOLV TN - Witco) | 4 |
| Polymer from Example 3 | 1 |
| Triethanolamine | 0.35 |
| Preservative and sequestrant | qs |
| Water | qs 100 |

EXAMPLE 9

Nail Varnish

| Polymer from Example 1 | 23.8 g of AS |
| --- | --- |
| Butyl acetate | 24.99 g |
| Isopropanol | 10.71 g |
| Hexylene glycol | 2.5 g |
| DC RED 7 Lake | 1 g |
| Hectorite modified with stearyldimethylbenzylammonium chloride (Bentone ® 27V from Elementis) | 1.3 g |

EXAMPLE 10

Mascara Composition

| Beeswax | 8 g |
| --- | --- |
| Paraffin wax | 3 g |
| Carnauba wax | 6 g |
| Hectorite modified with distearyldimethylbenzylammonium chloride (Bentone ® 38V from Elementis) | 5.3 g |
| Propylene carbonate | 1.7 g |
| Filler | 1 g |
| Pigments | 5 g |
| Polymer from Example 2 | 12 g of AS |
| Isododecane | qs 100 |

EXAMPLE 11

Mascara Composition

| | |
|---|---|
| Beeswax | 8 g |
| Paraffin wax | 3 g |
| Carnauba wax | 6 g |
| Hectorite modified with distearyldi-methylbenzylammonium chloride (Bentone ® 38V from Elementis) | 5.3 g |
| Propylene carbonate | 1.7 g |
| Filler | 1 g |
| Pigments | 5 g |
| Polymer from Example 4 | 12 g of AS |
| Isododecane | qs 100 |

EXAMPLE 12

Nail Varnish

| | |
|---|---|
| Polymer from Example 5 | 23.8 g of AS |
| Butyl acetate | 24.99 g |
| Isopropanol | 10.71 g |
| Hexylene glycol | 2.5 g |
| DC RED 7 Lake | 1 g |
| Hectorite modified with stearyldimethyl-benzylammonium chloride (Bentone ® 27V from Elementis) | 1.3 g |
| Ethyl acetate | qs 100 g |

EXAMPLE 13

Mascara Composition

| | |
|---|---|
| Beeswax | 8 g |
| Paraffin wax | 3 g |
| Carnauba wax | 6 g |
| Hectorite modified with distearyldi-methylbenzylammonium chloride (Bentone ® 38V from Elementis) | 5.3 g |
| Propylene carbonate | 1.7 g |
| Filler | 1 g |
| Pigments | 5 g |
| Polymer from Example 6 | 12 g of AS |
| Isododecane | qs 100 |

The invention claimed is:

1. A cosmetic composition comprising, in a cosmetically acceptable organic liquid medium, at least one non-elastomeric film-forming ethylenic linear block polymer and at least one gelling agent for the organic liquid medium,
   wherein the at least one non-elastomeric film-forming ethylenic linear block polymer has a polydispersity index of greater than or equal to 2.5 and comprises at least one first block and at least one second block of different theoretical glass transition temperatures (Tg),
   wherein the at least one first and at least one second blocks are linked together via an intermediate segment comprising at least one constituent monomer of the at least one first block and at least one constituent monomer of the at least one second block,
   wherein the at least one constituent monomer of the at least one first block differs from the at least one constituent monomer of the at least one second block, the intermediate segment is a random copolymer block, and the at least one first block of the polymer is chosen from:
   a) a block with a theoretical Tg of greater than or equal to 40° C.,
   b) a block with a theoretical Tg of less than or equal to 20° C.,
   c) a block with a theoretical Tg of between 20 and 40° C., and
   the at least one second block is chosen from a category a), b) or c) different from the at least one first block.

2. A cosmetic composition comprising, in a cosmetically acceptable organic liquid medium, at least one film-forming ethylenic linear block polymer free from styrene units, and at least one gelling agent for the organic liquid medium,
   wherein the at least one film-forming ethylenic linear block polymer free from styrene units has a polydispersity index of greater than or equal to 2.5 and comprises at least one first block and at least one second block of different theoretical glass transition temperatures (Tg),
   wherein the at least one first and at least one second blocks are linked together via an intermediate segment comprising at least one constituent monomer of the at least one first block and at least one constituent monomer of the at least one second block,
   wherein the at least one constituent monomer of the at least one first block differs from the at least one constituent monomer of the at least one second block, the intermediate segment is a random copolymer block, and the at least one first block of the polymer is chosen from:
   a) a block with a theoretical Tg of greater than or equal to 40° C.,
   b) a block with a theoretical Tg of less than or equal to 20° C.,
   c) a block with a theoretical Tg of between 20 and 40° C., and
   the at least one second block is chosen from a category a), b) or c) different from the at least one first block.

3. The cosmetic composition according to claim 1, wherein the at least one block polymer is chosen from ethylenic polymers derived from aliphatic ethylenic monomers comprising at least one ester group or at least one amide group.

4. The cosmetic composition according to claim 1, wherein the at least one block polymer is not soluble, at an amount of active substance of greater than or equal to 1% by weight, in water, or in a mixture of water and at least one alcohol chosen from linear and branched $C_2$ to $C_5$ monoalcohols, at ambient temperature of about 25° C. without a change in pH.

5. The cosmetic composition according to claim 1, wherein the at least one first block and at least one second block are incompatible in the organic liquid medium.

6. The cosmetic composition according to claim 1, wherein the intermediate segment has a theoretical glass transition temperature (Tg) between the theoretical glass transition temperatures of the at least one first block and at least one second block.

7. The cosmetic composition according to claim 1, wherein the block with a theoretical Tg of greater than or equal to 40° C. comprises at least one monomer whose corresponding homopolymer has a theoretical Tg of greater than or equal to 40° C.

8. The cosmetic composition according to claim 7, wherein the at least one monomer whose corresponding homopolymer has a theoretical Tg of greater than or equal to 40° C. is chosen from:

methacrylates of formula $CH_2$=$C(CH_3)$—$COOR_1$, wherein $R_1$ is chosen from linear and branched unsubstituted $C_1$ to $C_4$ alkyl groups and $C_4$ to $C_{12}$ cycloalkyl groups;
acrylates of formula $CH_2$=$CH$—$COOR_2$, wherein $R_2$ is chosen from $C_4$ to $C_{12}$ cycloalkyl groups and a tert-butyl group;
acrylamides of formula:

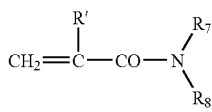

wherein $R_7$ and $R_8$, which may be identical or different, are each chosen from hydrogen atoms and linear and branched $C_1$ to $C_{12}$ alkyl groups; or, alternatively, $R_7$ is H and $R_8$ is a 1,1-dimethyl-3-oxobutyl group, and R' is H; and
methacrylamides of formula:

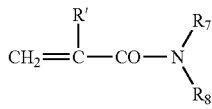

wherein $R_7$ and $R_8$, which may be identical or different, are each chosen from hydrogen atoms and linear and branched $C_1$ to $C_{12}$ alkyl groups; or, alternatively, $R_7$ is H and $R_8$ is a 1,1-dimethyl-3-oxobutyl group, and R' is methyl.

9. The cosmetic composition according to claim 8, wherein the at least one monomer whose corresponding homopolymer has a theoretical Tg of greater than or equal to 40° C. is chosen from methyl methacrylate, isobutyl acrylate, isobutyl methacrylate, isobornyl acrylate, and isobornyl methacrylate.

10. The cosmetic composition according to claim 1, wherein the at least one block with a theoretical Tg of less than or equal to 20° C. comprises at least one monomer whose corresponding homopolymer has a theoretical Tg of less than or equal to 20° C.

11. The cosmetic composition according to claim 10, wherein the at least one monomer whose corresponding homopolymer has a theoretical Tg of less than or equal to 20° C. is chosen from:
acrylates of formula $CH_2$=$CHCOOR_3$, wherein $R_3$ is chosen from linear and branched unsubstituted $C_1$ to $C_{12}$ alkyl groups, with the exception of the tert-butyl group, wherein at least one heteroatom chosen from O, N and S is optionally intercalated;
methacrylates of formula $CH_2$=$C(CH_3)$—$COOR_4$, wherein $R_4$ is chosen from linear and branched unsubstituted $C_6$ to $C_{12}$ alkyl groups, wherein at least one heteroatom chosen from O, N and S is optionally intercalated;
vinyl esters of formula $R_5$—$CO$—$O$—$CH$=$CH_2$, wherein $R_5$ is chosen from linear and branched $C_4$ to $C_{12}$ alkyl groups;
$C_4$ to $C_{12}$ alkyl vinyl ethers; and
N—($C_4$ to $C_{12}$ alkyl) acrylamides.

12. The cosmetic composition according to claim 11, wherein the at least one monomer whose corresponding homopolymer has a theoretical Tg of less than or equal to 20° C. is chosen from $C_1$ to $C_{10}$ alkyl acrylates, with the exception of tert-butyl acrylate.

13. The cosmetic composition according to claim 1, wherein the at least one block with a theoretical Tg of between 20° C. and 40° C. comprises at least one monomer whose corresponding homopolymer has a theoretical Tg of between 20° C. and 40° C.

14. The cosmetic composition according to claim 13, wherein the block with a theoretical Tg of between 20° C. and 40° C. comprises at least one monomer chosen from methyl methacrylate, isobornyl acrylate, isobornyl methacrylate, butyl acrylate, and 2-ethyihexyl acrylate.

15. The cosmetic composition according to claim 1, wherein the at least one block with a theoretical Tg of between 20° C. and 40° C. comprises (i) at least one monomer whose corresponding homopolymer has a theoretical Tg of greater than or equal to 40° C. and (ii) at least one monomer whose corresponding homopolymer has a theoretical Tg of less than or equal to 20° C.

16. The cosmetic composition according to claim 1, wherein the at least one first block has a theoretical Tg of greater than or equal to 40° C., and the at least one second block has a theoretical Tg of less than or equal to 20° C.

17. The cosmetic composition according to claim 16, wherein the at least one first block comprises at least one monomer whose corresponding homopolymer has a theoretical Tg of greater than or equal to 40° C.

18. The cosmetic composition according to claim 17, wherein the at least one first block is a copolymer comprising at least two monomers whose corresponding homopolymers have a theoretical Tg of greater than or equal to 40° C.

19. The cosmetic composition according to claim 17, wherein the at least one monomer whose corresponding homopolymer has a theoretical Tg of greater than or equal to 40° C. is chosen from:
methacrylates of formula $CH_2$=$C(CH_3)$—$COOR_1$, wherein $R_1$ is chosen from linear and branched unsubstituted $C_1$ to $C_4$ alkyl groups;
acrylates of formula $CH_2$=$CH$—$COOR_2$, wherein $R_2$ is chosen from $C_4$ to $C_{12}$ cycloalkyl groups;
acrylamides of formula:

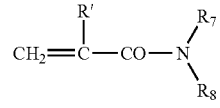

wherein $R_7$ and $R_8$, which may be identical or different, are each chosen from hydrogen atoms and linear and branched $C_1$ to $C_{12}$ alkyl groups; or, alternatively, $R_7$ is H and $R_8$ is a 1,1-dimethyl-3-oxobutyl group, and R' is H; and
methacrylamides of formula:

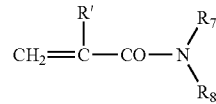

wherein $R_7$ and $R_8$, which may be identical or different, are each chosen from a hydrogen atom and linear and branched $C_1$ to $C_{12}$ alkyl groups; or $R_7$ is H and $R_8$ is a 1,1-dimethyl-3-oxobutyl group, and R' is methyl.

20. The cosmetic composition according to claim 18, wherein the at least one monomer whose corresponding homopolymer has a theoretical Tg of greater than or equal to 40° C. is chosen from methyl methacrylate, isobutyl methacrylate, isobornyl acrylate, and isobornyl methacrylate.

21. The cosmetic composition according to claim 17, wherein the at least one first block is present in an amount ranging from 20% to 90% by weight, relative to the total weight of the polymer.

22. The cosmetic composition according to claim 21, wherein the at least one first block is present in an amount ranging from 50% to 70% by weight, relative to the total weight of the polymer.

23. The cosmetic composition according to claim 16, wherein the at least one second block comprises at least one monomer whose corresponding homopolymer has a theoretical, Tg of less than or equal to 20° C.

24. The cosmetic composition according to claim 23, wherein the at least one second block is a homopolymer comprising a monomer whose corresponding homopolymer has a theoretical Tg of less than or equal to 20° C.

25. The cosmetic composition according to claim 23, wherein the at least one monomer whose corresponding homopolymer has a theoretical Tg of less than or equal to 20° C. is chosen from:
  acrylates of formula $CH_2$=$CHCOOR_3$, wherein $R_3$ is chosen from linear and branched unsubstituted $C_1$ to $C_{12}$ alkyl groups, with the exception of the tert-butyl group, wherein at least one heteroatom chosen from O, N and S is optionally intercalated;
  methacrylates of formula $CH_2$=$C(CH_3)$—$COOR_4$, wherein $R_4$ is chosen from linear and branched unsubstituted $C_6$ to $C_{12}$ alkyl groups, wherein at least one heteroatom chosen from O, N and S is optionally intercalated;
  vinyl esters of formula $R_5$—CO—O—CH=$CH_2$, wherein $R_5$ is chosen from linear and branched $C_4$ to $C_{12}$ alkyl groups;
  $C_4$ to $C_{12}$ alkyl vinyl ethers; and
  N—($C_4$ to $C_{12}$ alkyl) acrylamides.

26. The cosmetic composition according to claim 25, wherein the at least one monomer whose corresponding homopolymer has a theoretical Tg of less than or equal to 20° C. is chosen from alkyl acrylates whose alkyl chain comprises from 1 to 10 carbon atoms, with the exception of the tert-butyl group.

27. The cosmetic composition according to claim 16, wherein the at least one second block with a theoretical Tg of less than or equal to 20° C. is present in an amount ranging from 5% to 75% by weight, relative to the total weight of the polymer.

28. The cosmetic composition according to claim 27, wherein the at least one second block with a theoretical Tg of less than or equal to 20° C. is present in an amount ranging from 25% to 45% by weight, relative to the total weight of the polymer.

29. The cosmetic composition according to claim 1, wherein the at least one first block has a theoretical Tg of between 20° C. and 40° C., and the at least one second block has a theoretical Tg of less than or equal to 20° C. or a theoretical Tg of greater than or equal to 40° C.

30. The cosmetic composition according to claim 29, wherein the at least one first block with a theoretical Tg of between 20° C. and 40° C. comprises at least one monomer whose corresponding homopolymer has a theoretical Tg of between 20° C. and 40° C.

31. The cosmetic composition according to claim 29, wherein the at least one first block with a theoretical Tg of between 20° C. and 40° C. is a copolymer comprising (i) at least one monomer whose corresponding homopolymer has a theoretical Tg of greater than or equal to 40° C. and (ii) at least one monomer whose corresponding homopolymer has a theoretical Tg of less than or equal to 20° C.

32. The cosmetic composition according to claim 29, wherein the at least one first block with a theoretical Tg of between 20° C. and 40° C. comprises at least one monomer chosen from methyl methacrylate, isobornyl acrylate, isobornyl methacrylate, butyl acrylate, and 2-ethylhexyl acrylate.

33. The cosmetic composition according to claim 29, wherein the at least one first block with a theoretical Tg of between 20° C. and 40° C. is present in an amount ranging from 10% to 85% by weight, relative to the total weight of the polymer.

34. The cosmetic composition according to claim 33, wherein the at least one first block with a theoretical Tg of between 20° C. and 40° C. is present in an amount ranging from 50% to 70% by weight, relative to the total weight of the polymer.

35. The cosmetic composition according to claim 29, wherein the at least one second block has a theoretical Tg of greater than or equal to 40° C. and comprises at least one monomer whose corresponding homopolymer has a theoretical Tg of greater than or equal to 40° C.

36. The cosmetic composition according to claim 29, wherein the at least one second block has a theoretical Tg of greater than or equal to 40° C. and is a homopolymer comprising a monomer whose corresponding homopolymer has a theoretical Tg of greater than or equal to 40° C.

37. The cosmetic composition according to claim 35, wherein the at least one monomer whose corresponding homopolymer has a theoretical Tg of greater than or equal to 40° C. is chosen from:
  methacrylates of formula $CH_2$=$C(CH_3)$—$COOR_1$, wherein $R_1$ is chosen from linear and branched unsubstituted $C_1$ to $C_4$ alkyl groups and $C_4$ to $C_{12}$ cycloalkyl groups;
  acrylates of formula $CH_2$=CH—$COOR_2$, wherein $R_2$ is chosen from $C_4$ to $C_{12}$ cycloalkyl groups and a tert-butyl group;
  acrylamides of formula:

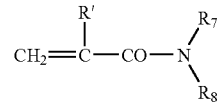

wherein $R_7$ and $R_8$, which may be identical or different, are each chosen from hydrogen atoms and linear and branched $C_1$ to $C_{12}$ alkyl groups; or, alternatively, $R_7$ is H and $R_8$ is 1,1-dimethyl-3-oxobutyl group, and R' is H; and
  methacrylamides of formula:

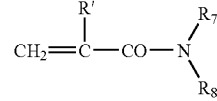

wherein $R_7$ and $R_8$, which may be identical or different, are each chosen from hydrogen atoms and linear and branched $C_1$ to $C_{12}$ alkyl groups; or, alternatively, $R_7$ is H and $R_8$ is 1,1-dimethyl-3-oxobutyl group, and R' is methyl.

38. The cosmetic composition according to claim 37, wherein the at least one monomer whose corresponding homopolymer has a theoretical Tg of greater than or equal to 40° C. is chosen from methyl methacrylate, isobutyl methacrylate, isobornyl acrylate, and isobornyl methacrylate.

39. The cosmetic composition according to claim 35, wherein the at least one second block with a theoretical Tg of greater than or equal to 40° C. is present in an amount ranging from 10% to 85% by weight, relative to the total weight of the polymer.

40. The cosmetic composition according to claim 39, wherein the at least one second block with a theoretical Tg of greater than or equal to 40° C. is present in an amount ranging from 30% to 70% by weight, relative to the total weight of the polymer.

41. The cosmetic composition according to claim 29, wherein the at least one second block has a theoretical Tg of less than or equal to 20° C. and comprises at least one monomer whose corresponding homopolymer has a theoretical Tg of less than or equal to 20° C.

42. The cosmetic composition according to claim 41, wherein the at least one second block is a homopolymer comprising a monomer whose corresponding homopolymer has a theoretical, Tg of less than or equal to 20° C.

43. The cosmetic composition according to claim 41, wherein the at least one monomer whose corresponding homopolymer has a theoretical Tg of less than or equal to 20° C. is chosen from:
   acrylates of formula $CH_2\!=\!CHCOOR_3$, wherein $R_3$ is chosen from linear and branched unsubstituted $C_1$ to $C_{12}$ alkyl groups, with the exception of the tert-butyl group, wherein at least one heteroatom chosen from O, N and S is optionally intercalated;
   methacrylates of formula $CH_2\!=\!C(CH_3)\!-\!COOR_4$, wherein $R_4$ is chosen from linear and branched unsubstituted $C_6$ to $C_{12}$ alkyl groups, wherein at least one heteroatom chosen from O, N and S is optionally intercalated;
   vinyl esters of formula $R_5\!-\!CO\!-\!O\!-\!CH\!=\!CH_2$, wherein $R_5$ is chosen from linear and branched $C_4$ to $C_{12}$ alkyl groups;
   $C_4$ to $C_{12}$ alkyl vinyl ethers; and
   $N\!-\!(C_4$ to $C_{12}$ alkyl) acrylamides.

44. The cosmetic composition according to claim 43, wherein the at least one monomer whose corresponding homopolymer has a theoretical Tg of less than or equal to 20° C. is chosen from $C_1$ to $C_{10}$ alkyl acrylates, with the exception of tert-butyl acrylate.

45. The cosmetic composition according to claim 41, wherein the at least one block with a theoretical Tg of greater than or equal to 40° C. is present in an amount ranging from 20% to 90% by weight, relative to the total weight of the polymer.

46. The cosmetic composition according to claim 45, wherein the at least one block with a theoretical Tg of greater than or equal to 40° C. is present in an amount ranging from 50% to 70% by weight, relative to the total weight of the polymer.

47. The cosmetic composition according to claim 1, wherein the at least one first block and/or the at least one second block comprises at least one additional monomer.

48. The cosmetic composition according to claim 47, wherein the at least one additional monomer is chosen from hydrophilic monomers and ethylenically unsaturated monomers comprising one or more silicon atoms.

49. The cosmetic composition according to claim 48, wherein the at least one additional monomer is chosen from:
   (a) hydrophilic monomers chosen from:
      ethylenically unsaturated monomers comprising at least one functional group chosen from carboxylic and sulphonic acid functional groups;
      ethylenically unsaturated monomers comprising at least one tertiary amine functional group;
      methacrylates of formula $CH_2\!=\!C(CH_3)\!-\!COOR_6$, wherein $R_6$ is chosen from linear and branched $C_1$ to $C_4$ alkyl groups substituted with at least one substituent chosen from hydroxyl groups and halogen atoms;
      methacrylates of formula $CH_2\!=\!C(CH_3)\!-\!COOR_9$, wherein $R_9$ is chosen from linear and branched $C_6$ to $C_{12}$ alkyl groups substituted with at least one substituent chosen from hydroxyl groups and halogen atoms, wherein at least one heteroatom chosen from O, N and S is optionally intercalated; and
      acrylates of formula $CH_2\!=\!CHCOOR_{10}$, wherein $R_{10}$ is chosen from
         (i) linear and branched $C_1$ to $C_{12}$ alkyl groups substituted with at least one substituent chosen from hydroxyl groups and halogen atoms, (ii) $C_1$ to $C_{12}$ alkyl-O-POE (polyoxyethylene), with repetition of the oxyethylene unit from 5 to 30 times, and (iii) a polyoxyethylenated group comprising from 5 to 30 ethylene oxide units; and
   b) ethylenically unsaturated monomers comprising at least one silicon atom.

50. The cosmetic composition according to claim 47, wherein each of the at least one first block and at least one second block comprises at least one additional monomer chosen from acrylic acid, methacrylic acid, and trifluoroethyl methacrylate.

51. The cosmetic composition according to claim 47, wherein each of the at least one first block and at least one second block comprises at least one additional monomer chosen from esters of acrylic acid and esters of methacrylic acid, and optionally at least one second additional monomer.

52. The cosmetic composition according to claim 47, wherein each of the at least one first block and at least one second block comprises at least one monomer chosen from esters of acrylic acid and esters of methacrylic acid, and optionally comprises at least one additional monomer.

53. The cosmetic composition according to claim 47, wherein the at least one additional monomer is present in an amount ranging from 1% to 30% by weight, relative to the total weight of the first and/or second blocks.

54. The cosmetic composition according to claim 1, wherein the difference between the theoretical glass transition temperatures of the at least one first block and at least one second block is greater than 10° C.

55. The cosmetic composition according to claim 54, wherein the difference between the theoretical glass transition temperatures of the at least one first block and at least one second block is greater than or equal to 40° C.

56. The cosmetic composition according to claim 1 wherein the at least one block polymer has a polydispersity index (I) of greater than or equal to 2.8.

57. The cosmetic composition according to claim 1, wherein the at least one block polymer has a polydispersity index (I) ranging from 2.8 to 6.

58. The cosmetic composition according to claim 1, wherein the at least one block polymer has a weight-average mass (Mw) of less than or equal to 300,000.

59. The cosmetic composition according to claim 58, wherein the at least one block polymer has a weight-average mass (Mw) ranging from 35,000 to 200,000.

60. The cosmetic composition according to claim 59, wherein the at least one block polymer has a weight-average mass (Mw) ranging from 45,000 to 150,000.

61. The cosmetic composition according to claim 58, wherein the at least one block polymer has a weight-average mass (Mw) that is less than or equal to 70,000.

62. The cosmetic composition according to claim 61, wherein the block polymer has a weight-average mass (Mw) ranging from 10,000 to 60,000.

63. The cosmetic composition according to claim 62, wherein the at least one block polymer has a weight-average mass (Mw) ranging from 12,000 to 50,000.

64. The cosmetic composition according to claim 1, wherein the at least one block polymer is present in a polymer active substance in an amount ranging from 0.1% to 60% by weight, relative to the total weight of the composition.

65. The cosmetic composition according to claim 64, wherein the at least one block polymer is present in a polymer active substance in an amount ranging from 10% to 40% by weight, relative to the total weight of the composition.

66. The cosmetic composition according to claim 1, wherein the at least one gelling agent is chosen from polymeric gelling agents.

67. The cosmetic composition according to claim 66, wherein the at least one polymeric gelling agent is chosen from crosslinked elastomeric polyorganosiloxanes of three-dimensional structure.

68. The cosmetic composition according to claim 67, wherein the crosslinked elastomeric polyorganosiloxanes of three-dimensional structure are chosen from MQ silicone resins, polyalkylsesquioxanes, and resins crosslinked by hydrosilylation.

69. The cosmetic composition according to claim 67, wherein the at least one polymeric gelling agent comprises at least one hydrophilic group.

70. The cosmetic composition according to claim 69, wherein the at least one hydrophilic group is chosen from polyoxyethylene and copoly(oxyethylene/oxypropylene) groups.

71. The cosmetic composition according to claim 66, wherein the at least one polymeric gelling agent is a silicone gum of formula:

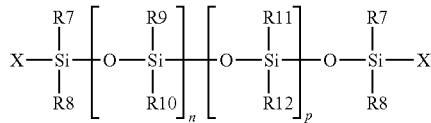

wherein $R_7$, $R8$, $R_{11}$ and $R_{12}$ may be identical or different, and each is chosen from $C_1$ to $C_6$ alkyl radicals;

$R_9$ and $R_{10}$ may be identical or different, and each is chosen from $C_1$ to $C_6$ alkyl radicals and aryl radicals;

X is chosen from $C_1$ to $C_6$ alkyl radicals, hydroxyl radicals, and vinyl radicals; and n and p are chosen so as to give the silicone gum a viscosity of greater than 100,000 mPa·s.

72. The cosmetic composition according to claim 71, wherein n and p are chosen so as to give the silicone gum a viscosity of greater than 500,000 mPa·s.

73. The cosmetic composition according to claim 66, wherein the at least one polymeric gelling agent is chosen from aminosilicone polymers having triazinyl groups or pyrimidinyl groups bonded to the amino groups of the aminosilicone polymers, nonsilicone polyamides whose ends carry ester or triamide functional groups, polyurethanes, and vinylic polymers carrying side groups that may give rise to mutual hydrogen interactions, acrylic polymers carrying side groups that may give rise to mutual hydrogen interactions, and methacrylic polymers carrying side groups that may give rise to mutual hydrogen interactions.

74. The cosmetic composition according to claim 66, wherein the at least one polymeric gelling agent is chosen from:
polystyrene-silicone and polyethylene-silicone copolymers;
copolymers comprising at least one silicone block and at least one other block or graft which is polyvinylic, polyacrylic, or polymethacrylic;
polymers and/or copolymers derived from the polymerization and/or copolymerization of at least one ethylenic monomer comprising at least one ethylenic bond; and
polymers and/or copolymers resulting from the polymerization and/or copolymerization of at least one ethylenic monomer comprising at least one styrene or at least one alkylstyrene block.

75. The cosmetic composition according to claim 74, wherein the ethylenic monomer comprising at least one ethylenic bond comprises at least one conjugated ethylenic bond.

76. The cosmetic composition according to claim 1, wherein the at least one gelling agent is fumed silica.

77. The cosmetic composition according to claim 1, wherein the at least one gelling agent is present in an amount ranging from 0.05% to 35% by weight, relative to the total weight of the composition.

78. The cosmetic composition according to claim 77, wherein the at least one gelling agent is present in an amount ranging from 1% to 10% by weight, relative to the total weight of the composition.

79. The cosmetic composition according to claim 1, further comprising at least one colorant chosen from water-soluble dyes and pulverulent colorants.

80. The cosmetic composition according to claim 79, wherein the at least one pulverulent colorant is chosen from pigments, nacres and flakes.

81. The cosmetic composition according to claim 1, wherein the composition is in the form of a suspension, dispersion, solution, gel, emulsion, cream, stick, mousse, dispersion of vesicles, two-phase lotion, multiphase lotion, spray, powder, or paste.

82. The composition according to claim 1, wherein it is in the form of a composition for making up or caring for keratin materials.

83. The cosmetic composition according to claim 82, wherein it is in the form of a lip makeup product.

84. The cosmetic composition according to claim 82, wherein it is in the form of an eye makeup product.

85. The cosmetic composition according to claim 82, wherein it is in the form of a complexion makeup product.

86. The cosmetic composition according to claim 82, where the cosmetic composition is in the form of a nail makeup product.

87. A cosmetic kit comprising:
(a) a container delimiting at least one compartment, the container being closed by a closing element; and
(b) a composition comprising, in a cosmetically acceptable organic liquid medium, at least one non-elastomeric film-forming ethylenic linear block polymer and at least one gelling agent for the organic liquid medium, disposed inside the compartment,
wherein the at least one non-elastomeric film-forming ethylenic linear block polymer has a polydispersity index of greater than or equal to 2.5 and comprises at least one first block and at least one second block of different theoretical glass transition temperatures (Tg),
wherein the at least one first and at least one second blocks are linked together via an intermediate segment comprising at least one constituent monomer of the at least one first block and at least one constituent monomer of the at least one second block,
wherein the at least one constituent monomer of the at least one first block differs from the at least one constituent monomer of the at least one second block, the intermediate segment is a random copolymer block, and the at least one first block of the polymer is chosen from:
a) a block with a theoretical Tg of greater than or equal to 40° C.,
b) a block with a theoretical Tg of less than or equal to 20° C.,
c) a block with a theoretical Tg of between 20 and 40° C., and
the at least one second block is chosen from a category a), b) or c) different from the at least one first block.

88. The cosmetic kit according to claim 87, wherein the container is formed, at least partly, of at least one thermoplastic material.

89. The cosmetic kit according to claim 87, wherein the container is formed, at least partly, of at least one non-thermoplastic material.

90. The cosmetic kit according to claim 87, wherein, in the closed position of the container, the closing element is screwed onto the container.

91. The cosmetic kit according to claim 87, wherein, in the closed position of the container, the closing element is coupled to the container other than by screwing.

92. The cosmetic kit according to claim 87, wherein the composition is substantially at atmospheric pressure inside the compartment.

93. The cosmetic kit according to claim 87, wherein the composition is pressurized inside the container.

94. A cosmetic method of making up or caring for keratin materials, comprising applying to the keratin materials a cosmetic composition comprising, in a cosmetically acceptable organic liquid medium, at least one non-elastomeric film-forming ethylenic linear block polymer and at least one gelling agent for the organic liquid medium,
wherein the at least one non-elastomeric film-forming ethylenic linear block polymer has a polydispersity index of greater than or equal to 2.5 and comprises at least one first block and at least one second block of different theoretical glass transition temperatures (Tg),
wherein the at least one first and at least one second blocks are linked together via an intermediate segment comprising at least one constituent monomer of the at least one first block and at least one constituent monomer of the at least one second block,
wherein the at least one constituent monomer of the at least one first block differs from the at least one constituent monomer of the at least one second block, the intermediate segment is a random copolymer block, and the at least one first block of the polymer is chosen from:
a) a block with a theoretical, Tg of greater than or equal to 40° C.,
b) a block with a theoretical Tg of less than or equal to 20° C.,
c) a block with a theoretical Tg of between 20 and 40° C., and
the at least one second block is chosen from a category a), b) or c) different from the at least one first block.

95. A cosmetic composition comprising, in a cosmetically acceptable organic liquid medium:
(a) at least one film-forming ethylenic linear block polymer; and
(b) at least one gelling agent for the organic liquid medium, chosen from:
fumed silica,
polystyrene-silicone and polyethylenesilicone copolymers,
copolymers comprising at least one silicone block and at least one other block or graft which is chosen from polyvinylic, polyacrylic, and polymethacrylic blocks,
polymers and/or copolymers resulting from the polymerization and/or copolymerization of at least one ethylenic monomer containing at least one ethylenic bond, and
polymers and/or copolymers resulting from the polymerization and/or copolymerization of at least one ethylenic monomer comprising at least one styrene or at least one alkyistyrene block,
wherein the at least one film-forming ethylenic linear block polymer has a polydispersity index of greater than or equal to 2.5 and comprises at least one first block and at least one second block of different theoretical glass transition temperatures (Tg),
wherein the at least one first and at least one second blocks are linked together via an intermediate segment comprising at least one constituent monomer of the at least one first block and at least one constituent monomer of the at least one second block,
wherein the at least one constituent monomer of the at least one first block differs from the at least one constituent monomer of the at least one second block, the intermediate segment is a random copolymer block, and the at least one first block of the polymer is chosen from:
a) a block with a theoretical Tg of greater than or equal to 40° C.,
b) a block with a theoretical Tg of less than or equal to 20° C.,
c) a block with a theoretical Tg of between 20 and 40° C., and
the at least one second block is chosen from a category a), b) or c) different from the at least one first block.

* * * * *